US010453555B2

(12) United States Patent
Janes et al.

(10) Patent No.: US 10,453,555 B2
(45) Date of Patent: Oct. 22, 2019

(54) PARAMETERIZING CELL-TO-CELL REGULATORY HETEROGENEITIES VIA STOCHASTIC TRANSCRIPTIONAL PROFILES

(71) Applicant: University of Virginia Patent Foundation, Charlottesville, VA (US)

(72) Inventors: Kevin Janes, Richmond, VA (US); Sameer Bajikar, Missouri City, TX (US); Fabian Theis, Garching (DE); Christiane Fuchs, Munich (DE)

(73) Assignee: University of Virginia Patent Foundation, Charlottesville, VA (US)

( * ) Notice: Subject to any disclaimer, the term of this patent is extended or adjusted under 35 U.S.C. 154(b) by 710 days.

(21) Appl. No.: 15/000,448

(22) Filed: Jan. 19, 2016

(65) Prior Publication Data

US 2016/0253453 A1   Sep. 1, 2016

Related U.S. Application Data

(60) Provisional application No. 62/269,246, filed on Dec. 18, 2015, provisional application No. 62/104,279, filed on Jan. 16, 2015.

(51) Int. Cl.
*G06F 19/20* (2011.01)
*G16B 25/00* (2019.01)
*G16B 5/00* (2019.01)

(52) U.S. Cl.
CPC ............... *G16B 25/00* (2019.02); *G16B 5/00* (2019.02)

(58) Field of Classification Search
CPC ............ C12Q 2600/158; C12Q 1/6809; C12Q 2600/118; C12Q 1/6883; C12Q 2600/136;
(Continued)

(56) References Cited

U.S. PATENT DOCUMENTS 8,586,305 B2 * 11/2013 Gurtner ............... C12Q 1/6876
435/378

FOREIGN PATENT DOCUMENTS

WO   WO2011/084643   * 7/2011

OTHER PUBLICATIONS

Wang, L. et al. 2013 Nature Protocols vol. 8 No. 2 pp. 282-301. 2013.*

(Continued)

*Primary Examiner* — Mary K Zeman
(74) *Attorney, Agent, or Firm* — Finnegan, Henderson, Faraborw, Garrett & Dunner LLP

(57) ABSTRACT

Regulated changes in gene expression underlie many biological processes, but globally profiling cell-to-cell variations in transcriptional regulation is problematic when measuring single cells. Transcriptome-wide identification of regulatory heterogeneities can be robustly achieved by randomly collecting small numbers of cells followed by statistical analysis. However, this stochastic-profiling approach blurs out the expression states of the individual cells in each pooled sample. Various aspects of the disclosure show that the underlying distribution of single-cell regulatory states can be deconvolved from stochastic-profiling data through maximum-likelihood inference. Guided by the mechanisms of transcriptional regulation, the disclosure provides mixture models for cell-to-cell regulatory heterogeneity which result in likelihood functions to infer model parameters. Inferences that validate both computationally and experimentally different mixture models, which include regulatory states for multicellular function occupied by as few as one in 40 cells of the population, are also encompassed. When the disclosed method extends to programs of heterogeneously coexpressed transcripts, the population-level inferences are much more accurate with pooled samples than with one-cell (Continued)

samples when the extent of sampling was limited. The disclosed deconvolution method provides a means to quantify the heterogeneous regulation of molecular states efficiently and gain a deeper understanding of the heterogeneous execution of cell decisions.

**18 Claims, 24 Drawing Sheets
(11 of 24 Drawing Sheet(s) Filed in Color)**

(58) Field of Classification Search
CPC .............. C12Q 1/025; C12Q 2600/142; C12Q 2600/156; C12Q 1/6806; C12Q 1/68; C12Q 1/6876; C12Q 1/6881; C12Q 2537/165; G06F 19/24; G06F 19/18; G06F 19/20; G06F 19/22; G06F 19/28; G06F 19/12; G06F 19/3456; G06F 17/30371; G06F 17/30598; G06F 19/00; G06F 19/14; G06F 17/18; G16H 10/20; G16H 10/60; G16H 50/70; G16H 50/50; G16H 80/00; A61B 5/0071; G06K 9/00147; G06K 9/6269; G06K 9/6276; G06K 19/06; G06N 7/005; G01N 2800/52; G01N 33/5047; G01N 33/5023; G01N 2800/50; G16B 25/00; G16B 30/00; G16B 20/00; G16B 25/10; G16B 30/10; G16B 40/00; G16B 50/00; G16B 5/00

See application file for complete search history.

(56) References Cited

OTHER PUBLICATIONS

Janes, K. A. et al Nature Methods 2010 vol. 7 No. 4 pp. 311-317. 2010.*

* cited by examiner

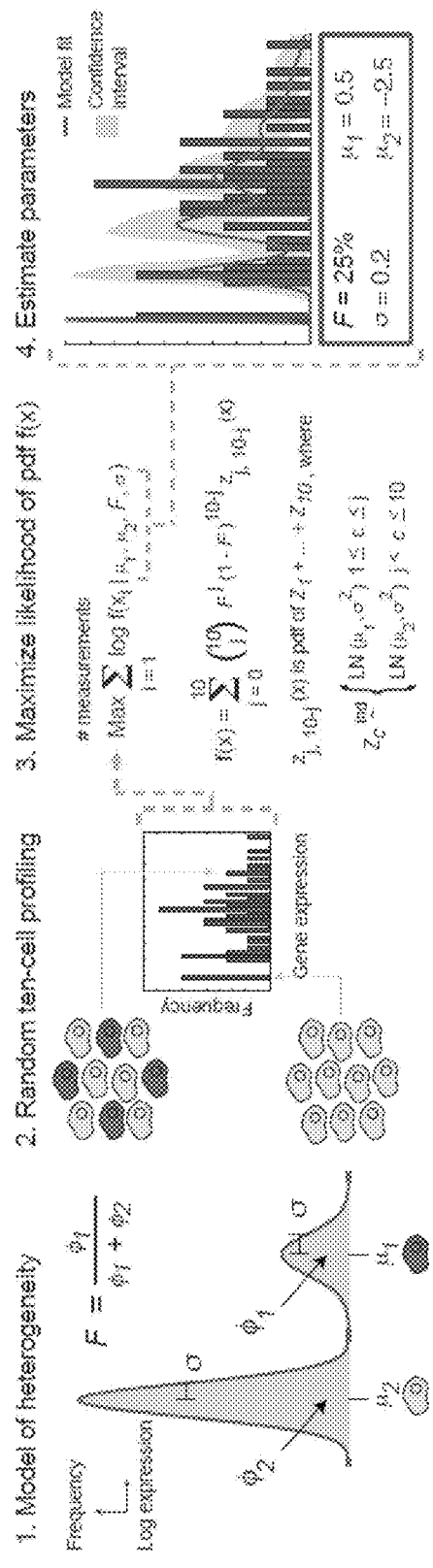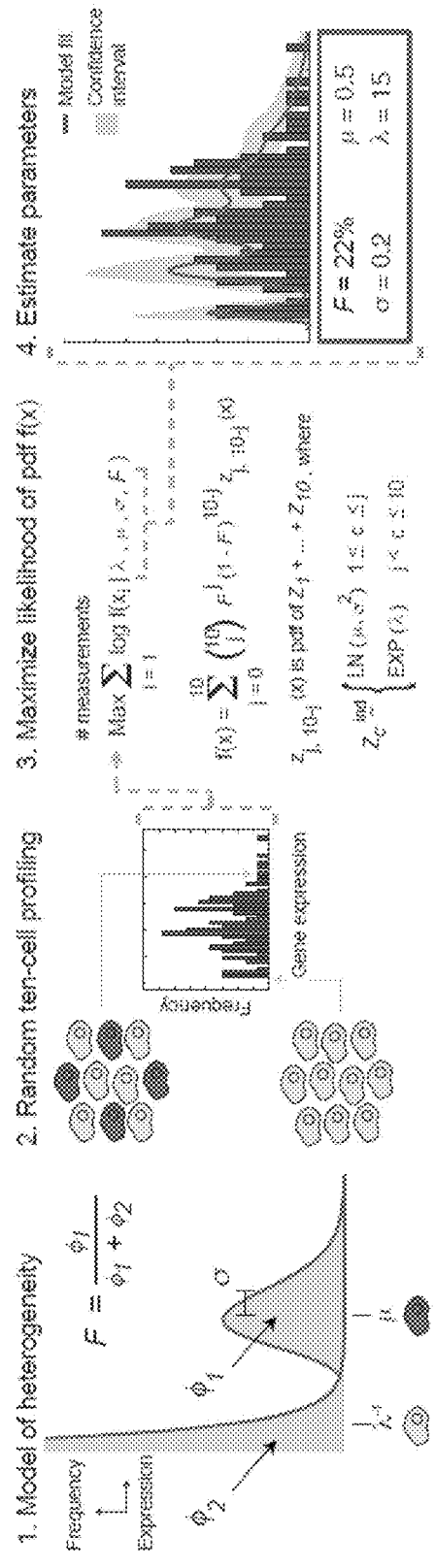
FIG. 3A
FIG. 3B

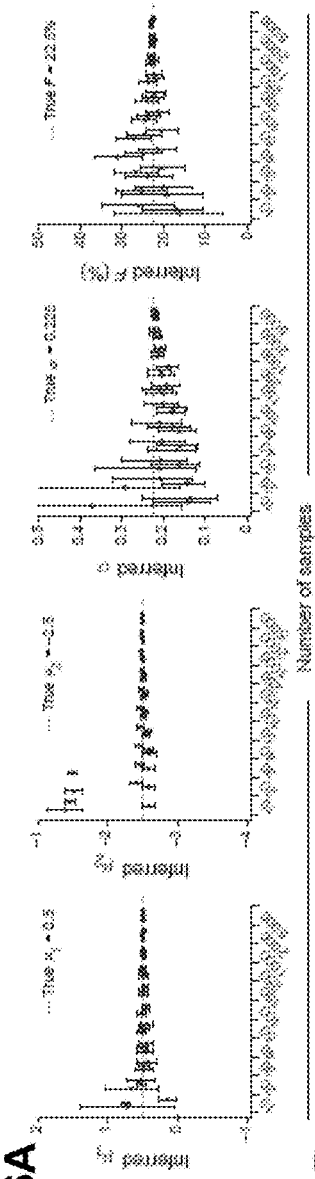
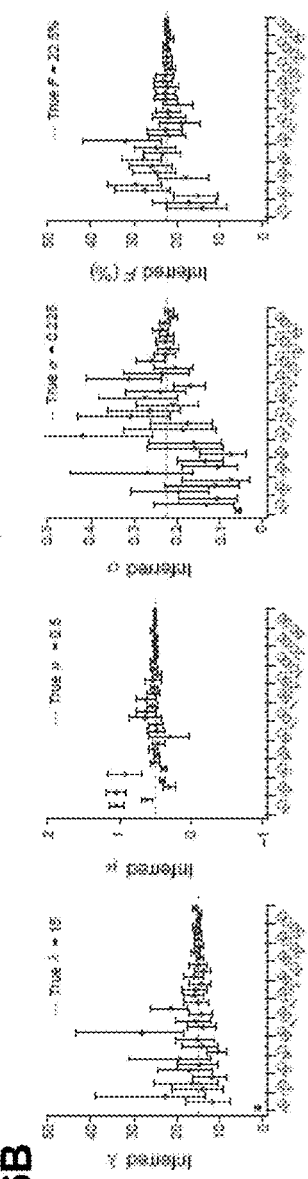
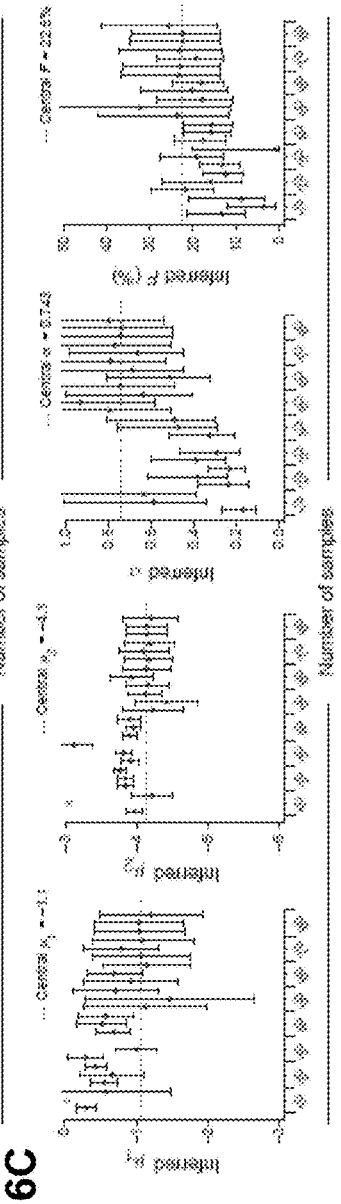
FIG. 6A
FIG. 6B
FIG. 6C

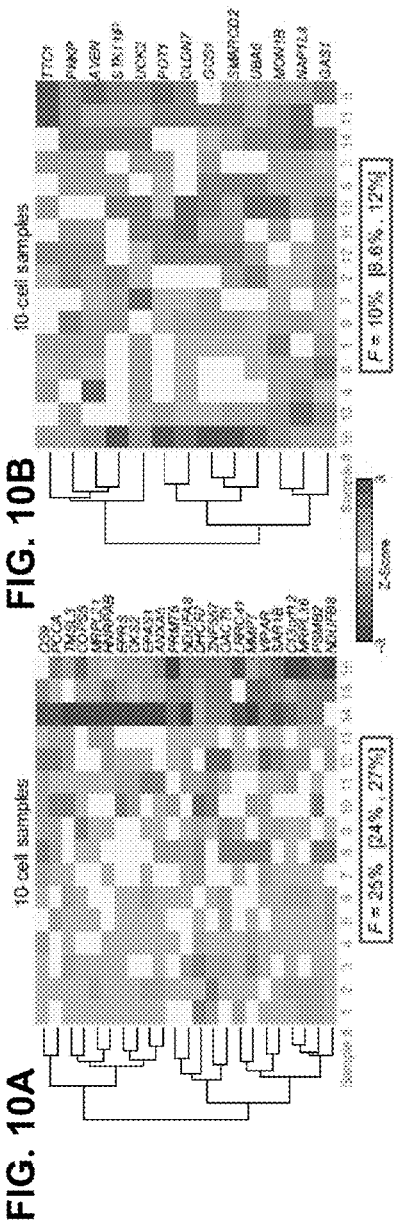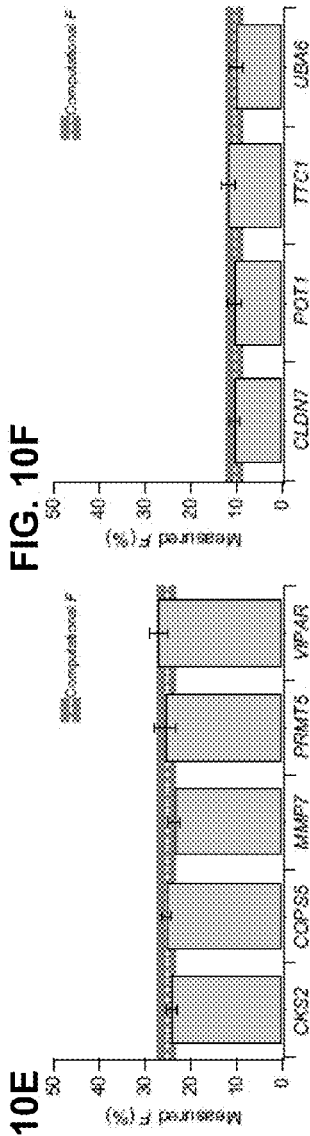
FIG. 10A
FIG. 10B
FIG. 10C
FIG. 10D
FIG. 10E
FIG. 10F

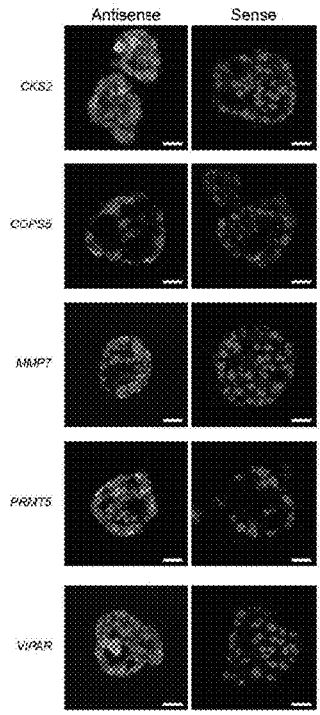
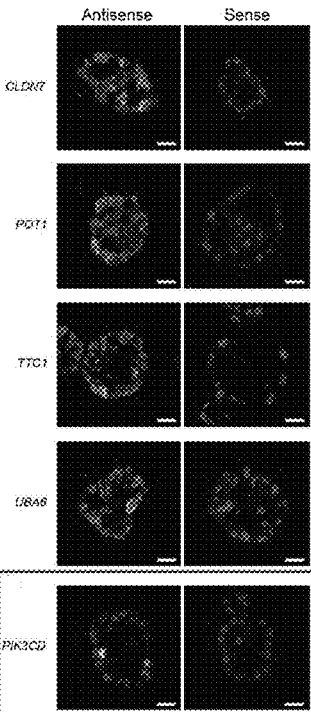
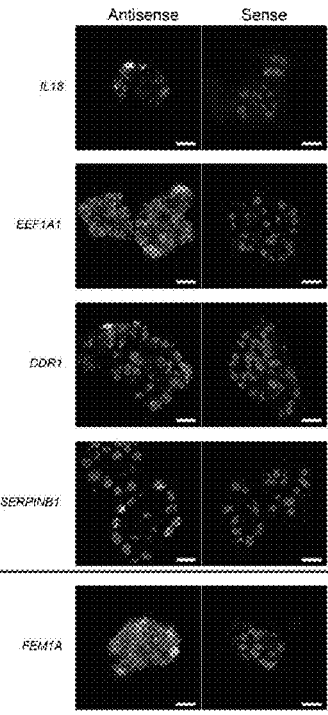
FIG. 13A  FIG. 13B  FIG. 13C
FIG. 13D

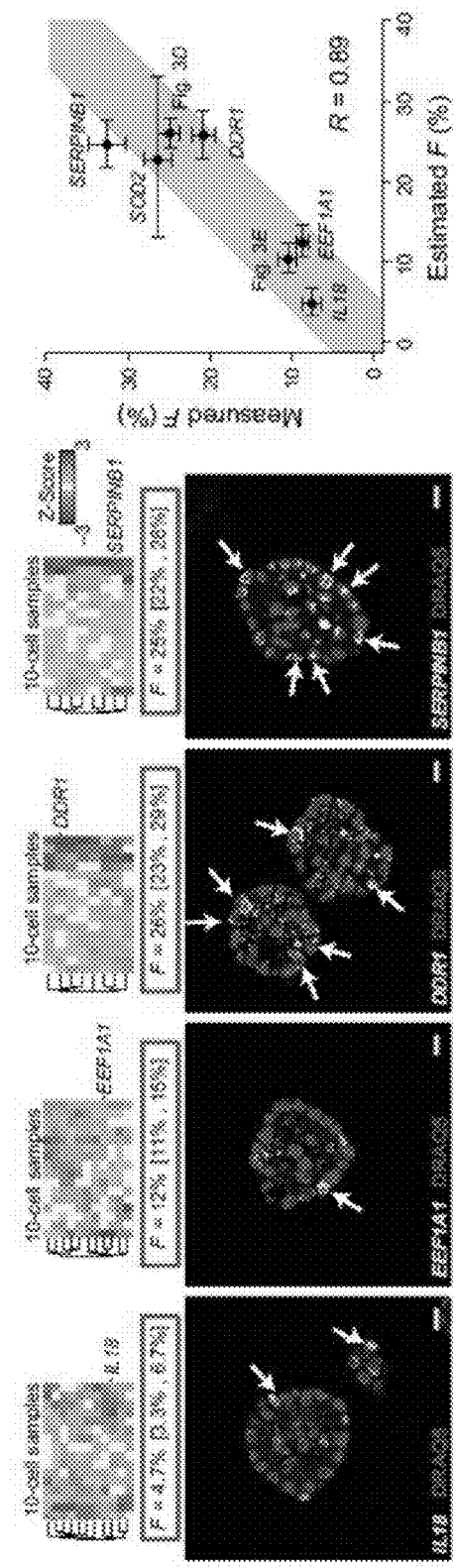

PARAMETERIZING CELL-TO-CELL REGULATORY HETEROGENEITIES VIA STOCHASTIC TRANSCRIPTIONAL PROFILES

RELATED APPLICATIONS

This application claims priority under 35 U.S.C. § 119(e) to U.S. Provisional Application Ser. No. 62/104,279 filed Jan. 16, 2015 and U.S. Provisional Application Ser. No. 62/269,246 filed Dec. 18, 2015. These applications are herein incorporated fully by reference.

FIELD

The present disclosure provides methods for inferring expression characteristics of single genes and gene clusters from small groups of cells.

BACKGROUND

Cell-to-cell differences in transcriptional or posttranslational regulation can give rise to heterogeneous phenotypes within a population (Slack et al. (2008) Proc Natl Acad Sci U.S.A. 105(49):19306-19311; Raj et al. (2010) Nature 463 (7283):913-918; Singh et al. (2010) Mol Syst Biol 6:369; Wernet et al. (2006) Nature 440(7081):174-180; Laslo et al. (2006) Cell 126(4):755-766; Gupta et al. (2011) Cell 146 (4):633-644; Tyson et al. (2012) Nat Methods 9(9):923-928). These changes in gene expression drive many biological processes. There are several techniques for monitoring regulatory states in single cells after a network of marker and effector genes has been identified (Loo et al. (2009) Nat Methods 6(10):759-765; Dalerba et al. (2011) Nat Biotechnol 29(12):1120-1127; Taniguchi et al. (2009) Nat Methods 6(7):503-506; Bendall et al. (2011) Science 332(6030):687-696; Raj et al. (2008) Nat Methods 5(10):877-879; Lubeck et al. (2012) Nat Methods 9(7):743-748). However, the options are much more limited when seeking to discover novel states without a predefined network.

At the transcript level, global methods have been developed to profile single cells by oligonucleotide microarrays (Kurimoto et al. (2006) Nucleic Acids Res 34(5):e42; Tietjen et al. (2003) Neuron 38(2):161-175) or RNA-seq (Hashimshony et al. (2012) Cell Rep 2(3):666-673; Ramskold et al. (2012) Nat Biotechnol 30(8):777-782; Tang et al. (2009) Nat Methods 6(5):377-382; Shalek et al. (2013) Nature 498 (7453):236-240). But generally, such approaches overlook the considerable technical variation in RNA extraction and reverse-transcription when applied to the limited starting material of single cells (Wang et al. (2013) Nat Protoc 8(2):282-301; Reiter et al. (2011) Nucleic Acids Res 39(18): e124). Single-cell profiles also retain the biological noisiness associated with each cell's isolation and handling (Hansen et al. (2011) Nat Biotechnol 29(7):572-573). These confounding sources of variation cannot be separated from reproducible heterogeneities in regulation unless many (>50) cells are individually profiled (Dalerba et al. (2011) Nat Biotechnol 29(12):1120-1127). Therefore, challenges remain for single-cell methods to discover regulatory heterogeneities in a reliable, unbiased, and efficient way.

An attractive alternative to single-cell methods is to analyze sets of population-averaged data and define regulatory signatures for discrete subpopulations. Existing approaches for transcriptomic data are able to deconvolve mixed cellular states computationally, but they require hundreds of coexpressed markers or calibration with purified cell populations (Riedel et al. (2013) Phys Rev E 87(4): 042715; Shen-Orr et al. (2010) Nat Methods 7(4):287-289; Gong et al. (2011) PLoS One 6(11):e27156). Usually, the size or identity of regulatory states is not defined beforehand and their discovery is what motivates the study (Dalerba et al. (2011) Biotechnol 29(12):1120-1127; Bendall et al. (2011) Science 332(6030):687-696; Loo et al. (2009) J Cell Biol 187(3):375-384). Certain states may also lack well-defined surface markers that would allow purification, it thus remains unclear whether computational inference with multiple cell averages can track quantitative characteristics of regulatory states not previously thought to exist.

As a hybrid between single-cell and mixture-based approaches, a technique that applies probability theory to transcriptome-wide measurements was developed (Janes et al. (2010) Nat Methods 7(4):311-317). The method begins with random collections of up to 10 cells isolated in situ where cell-to-cell regulatory heterogeneities could possibly reside. Each of these "stochastic samples" is then profiled for overall mRNA expression by using a heavily customized cDNA amplification procedure together with oligonucleotide microarrays (Wang et al. (2013) Nat Protoc 8(2):282-301). The process of random sampling is repeated 15-20 times to build a distribution of 10-cell averages. Transcripts with stark cell-to-cell variations can be distinguished statistically because of binomial fluctuations in single-cell expression that convolve their 10-cell averages. Last, candidate heterogeneities are clustered on a gene-by-gene basis according to the patterns of their sampling fluctuations to indicate putative regulatory states in single cells (Janes et al. (2010) Nat Methods 7(4):311-317).

Stochastic-profiling experiments are quantitative and highly reproducible as a result of the 10-fold increase in starting material compared to a single cell (Wang et al. (2013) Nat Protoc 8(2):282-301). However, a recognized drawback of the approach is that explicit information about single cells is "lost" in the 10-cell averages. While the transcriptome-wide identification of regulatory heterogeneities can be robustly achieved by randomly collecting small numbers of cells, the method blurs out the expression state of individual cells in each sample and thus, does not give an entirely accurate representation. There remains a need for acquiring quantitative, single-cell data from measurements that are not collected from single cells. Improved methods that can be applied to any type of biomolecule measured with a bioassay that is sensitive to tens of cells may lead to discovering regulatory heterogeneities in a number of biological contexts, such as development and cancer. A clear and quantified understanding of gene expression regulation would give scientists vital information for the development of therapies in every indication. Further, quantifying single-cell regulatory heterogeneities while avoiding the measurement noise of global single-cell techniques will he particularly relevant to solid tissues, where single-cell dissociation and molecular profiling is especially problematic.

SUMMARY

The present disclosure provides a method of recovering single-cell expression characteristics computationally and reconstructing the single-cell distribution of regulatory states. The present disclosure provides a method for inferring single-cell gene expression characteristics from a distribution of expression data of one or more individual genes in samples each comprising more than one cell. In some embodiments, the method comprises providing a model of heterogeneous gene regulation. In one embodiment, the model of heterogeneous gene regulation comprises a mixture of two regulatory states. In one embodiment, the method further comprises applying a maximum-likelihood inference to infer the single-cell gene expression characteristics for an individual gene.

In some embodiments, the two regulator states of an individual gene are characterized as a basal state and an induced regulatory state. In one embodiment, the basal state and induced regulatory state can each be approximated by a lognormal distribution. In another embodiment, the basal state can be approximated by an exponential distribution and the induced regulatory state can be approximated by a lognormal distribution.

In some embodiments, the two lognormal regulatory states can be characterized by the following parameters: the log-mean expression of the basal regulatory state, the log-mean expression of the induced regulatory state, the common log-standard deviation of the basal state and the induced regulatory state, and the probability that a single cell belongs in the induced regulatory state. In one embodiment, the log-standard deviation of the basal state and the log-standard deviation of the induced regulatory state are not common but are instead individual parameters.

In one embodiment, the basal exponential state and the induced lognormal regulatory state can be characterized by the following parameters: the rate parameter for the basal regulatory state, the log-mean expression of the induced regulatory state, the common log-standard deviation of the basal state and the induced regulatory state, and the probability that a single cell belongs in the induced regulatory state.

In some embodiments, the method further comprises inferring the regulatory state parameters by the maximum-likelihood inference of the present disclosure, providing inference of the individual gene expression characteristics.

In some embodiments the number of cells in each sample is 10. In other embodiments, the number of samples is at least 50-100. In one embodiment, the number of samples is at least 50.

The present disclosure also provides a method of inferring expression characteristics of a gene cluster from a distribution of expression data of a gene cluster.

In some embodiments, the basal state and induced regulatory state can each be approximated by a lognormal distribution. In one embodiment, the individual genes of the cluster can be characterized by the log-mean expression of an individual gene in the basal regulatory state and the log-mean expression of an individual gene in the induced regulatory state. In one embodiment, the genes of the gene cluster share a common log-standard deviation of the regulatory states and a common probability that a single cell belongs in the induced regulatory state.

In some embodiments, the basal state can be approximated by an exponential distribution and the induced regulatory state can be approximated by a lognormal distribution. In one embodiment, the individual genes of the cluster can be characterized by the rate parameter of an individual gene in the basal regulatory state and the long-mean expression of an individual gene in the induced regulatory state. In one embodiment, the genes of the acne cluster share a common log-standard deviation of the regulatory states and a common probability that a single cell belongs in the induced regulatory state.

In some embodiments, the method further comprises inferring the regulatory state parameters by the maximum-likelihood inference of the present disclosure, providing inference of the expression characteristics of the gene cluster.

In one embodiment, the number of samples is less than 50. In another embodiment, the number of samples is at least 50.

In one embodiment, the gene cluster is broken down into four-gene subgroups to infer log-means for each gene in the subgroup and local estimates of the log-standard deviation of the regulatory states and the probability that a single cell belongs in the induced regulatory state. In another embodiment, the gene cluster is broken down into four-gene subgroups to infer log-means for each gene in the subgroup and local estimates of the rate parameter for the basal regulatory state, log-standard deviation of the regulatory states, and the probability that a single cell belongs in the induced regulatory state.

In some embodiments, the method further comprises approximating confidence intervals of the inferred parameters.

In some embodiments, the method is used to infer single-cell gene expression characteristics of solid samples. In one embodiment, the solid sample can be a cancer. In some embodiments, the inferred expression characteristics can be applied to the development of therapies.

The disclosure further comprises a system for implementing the disclosed methods.

BRIEF DESCRIPTION OF THE DRAWINGS

The patent or application file contains at least one drawing executed in color. Copies of this patent or patent application with color drawing(s) will be provided by the Office upon request and payment of the necessary fee.

FIG. 3A shows the four steps of the maximum-likelihood approach where inference of stochastic 10-cell samples is made from an LN-LN mixture of regulatory states.

FIG. 3B shows the four steps of the maximum-likelihood approach where inference of a near-silent, exponential regulatory state and lognormal regulatory state is made.

FIG. 6A shows that parameter accuracy and confidence stabilizes with 50-100 random 10-cell samples. 10-cell expression data were computational simulated at fixed parameters: $\mu_1=0.5$, $\mu_2=-2.5$, F=22.5%, and $\sigma=0.225$, gray dashed for the LN-LN mixture.

FIG. 6B shows that parameter accuracy and confidence stabilizes with 50-100 random 10-cell samples. 10-cell expression data were computational simulated at fixed parameters: $\lambda=15$, $\mu_1=0.5$, F=22.5%, and $\sigma=0.225$, gray dashed for the EXP-LN mixture.

FIG. 6C shows that parameter accuracy and confidence stabilizes with 50-100 random 10-cell samples. The number of 10-cell samples varied from 10 to 5000.

FIG. 10A shows one example of a heat map of clustered 10-cell transcriptional profiles.

FIG. 10B shows another example of a heat heatmap of clustered 10-cell transcriptional profiles.

FIG. 10C shows representative RNA FISH images of transcripts from the infrequent cluster.

FIG. 10D shows representative RNA FISH images of transcripts from the rare cluster.

FIG. 10E shows a percentage of cells showing high expression by RNA FISH (gray bar) of one subset of genes in each cluster compared with the maximum-likelihood estimate of F.

FIG. 10F shows a percentage of cells showing high expression by RNA FISH (gray bar) of another subset of genes in each cluster compared with the maximum-likelihood estimate of F.

FIG. 13A shows fluorescence intensities from RNA FISH are specific to endogenous transcripts. Probe validations are for genes in the infrequent cluster.

FIG. 13B shows fluorescence intensities from RNA FISH are specific to endogenous transcripts. Probe validations are for genes in the the rare cluster.

FIG. 13C Shows fluorescence intensities from RNA FISH are specific to endogenous transcripts. Probe validations are for genes in the the assorted clusters.

FIG. 13D shows fluorescence intensities from RNA FISH are specific to endogenous transcripts. Probe validations are for genes in the the very-rare cluster.

FIG. 15A shows clusters of 10-cell expression fluctuations among ECM-attached cells for IL18.

FIG. 15B shows clusters of 10-cell expression fluctuations among ECM-attached cells for EEF1A1.

FIG. 15C shows clusters of 10-cell expression fluctuations among ECM-attached cells for DDR1.

FIG. 15D shows clusters of 10-cell expression fluctuations among ECM-attached cells for SERPINB1.

FIG. 15E shows the percentage of cells scored for high expression by RNA FISH compared with the maximum-likelihood estimate of F.

DETAILED DESCRIPTION

Figure 1A:
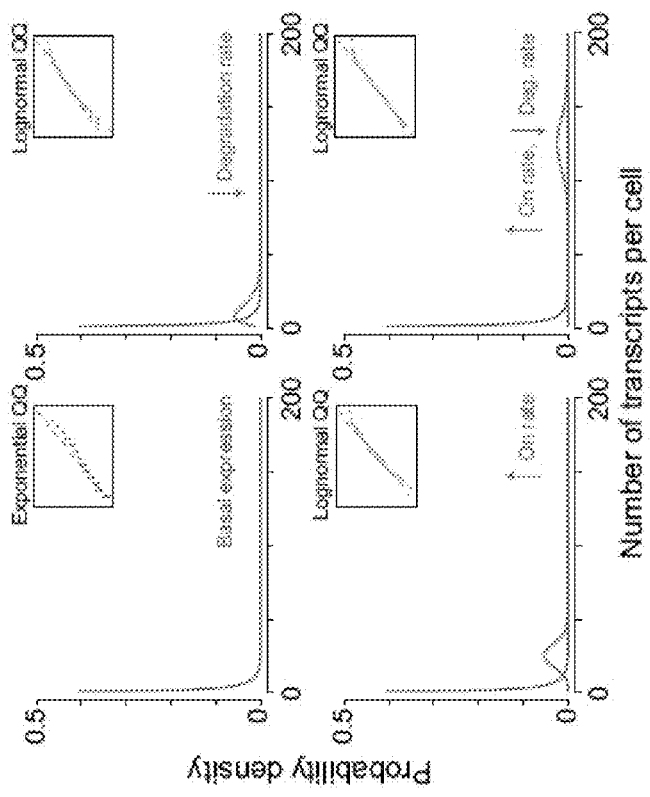
FIG. 1A shows probability densities for the number of transcripts per cell using a kinetic model having parameters that led to basal regulatory states (blue) with nonzero copies per cell.

The following detailed description and examples illustrate certain embodiments of the present disclosure. Those of skill in the art will recognize that there are numerous variations and modifications of this disclosure that are encompassed by its scope. Accordingly, the description of certain embodiments should not be deemed as limiting.

All references cited herein, including, but not limited to, published and unpublished applications, patents, and literature references, are incorporated herein by reference in their entirety and are hereby made a part of this specification.

This disclosure provides methods of inferring expression characteristics of single genes and gene clusters by mathematically deconvolving global measurements taken from small groups of cells. Various aspects of the disclosure relate to recovering this information computationally and reconstructing the single-cell distribution of regulatory states. Methods that combine maximum-likelihood estimations with mixture models that are grounded in known mechanisms of transcriptional regulation are also disclosed. The disclosure also provides maximum-likelihood inferences that quantify the single-cell characteristics of each regulatory state, including the probability that a cell will reside in one state or the other. In a further embodiment, the predictions are validated with independent gene-specific observations in single cells. According to certain embodiments, when sampling is limited to fewer than 20 observations, the parameterization of regulatory states is more accurate when given 10-cell data compared to one cell data.

According to certain embodiments, a probabilistic model of gene expression that is biologically accurate is used to make single-cell inferences. In certain embodiments, a method is provided that considers genes that exhibit two distinct regulatory states in a population of cells (See, for example, FIG. 1). In a further embodiment, the cell-to-cell variation of expression within each state is described by a lognormal distribution according to measurements of high-copy transcripts in single mammalian cells. In some embodiments, the model of gene expression is derived based on the kinetics of polymerase binding-unbinding, transcriptional elongation, and mRNA degradation (See, for example, FIG. 2). In another embodiment, the relative magnitudes of the kinetic rate parameters together govern the steady-state distribution of transcripts in the population, allowing different regulatory states to be simulated.

In some embodiments, the parameter sets for the number of transcripts include nonzero copies per cell. In a further embodiment, the lognormal distribution is a suitable approximation of basal expression. In certain embodiments, parameter sets yielding median expression levels as low as 20 copies per cell show minor skewness in quantile-quantile (QQ) comparisons with a lognormal distribution. In some embodiments, a second cellular regulatory state may be simulated by increasing the rate of polymerase binding, decreasing the rate of mRNA degradation, or both. In another embodiment, a second regulatory state may be simulated by mRNA stabilization that occurs posttranscriptionally through dedicated signal-transduction pathways activated by environmental stresses and proinflammatory stimuli. In a preferred embodiment, simulations of gene upregulation lead to right-shifted distributions that are lognormal. In a further embodiment, lognormal random variables are appropriate for the regulated expression of mid- to high-abundance transcripts.

In some embodiments, the parameter sets for the number of transcripts include near-zero copies per cell. In a further embodiment, the regulatory state is best captured by an exponential distribution. In a further embodiment, when kinetic parameters of a basal exponential state are modified to create a second right-shifted state, the resulting distributions are lognormal.

In certain embodiments, the single-cell regulatory heterogeneities can be depicted as a mixture of two lognormal states or as a mixture of an exponential state and a lognormal state. In some embodiments, the mixture gives rise to a probability distribution characterized by four key parameters. In some embodiments, the lognormal-lognormal (LN-LN) mixture requires the log-mean expression of the two regulatory states ($\mu_1$, $\mu_2$), the common log-standard deviation for biological noise ($\sigma$), and the expression frequency (F) describing the probability that cells will occupy the higher regulatory state (See, for example, FIG. 3A). In a further embodiment, a gene that is expressed at an ~8 fold higher level in 20% of the population with a coefficient of variation (CV) of ~50% is captured by $\mu_1-\mu_2=2$, F=20%, and $\sigma=0.48$. In other embodiments, the two regulatory states are characterized by separate log-standard deviations $\sigma_1$ and $\sigma_2$ in a "relaxed LN-LN" mixture.

In certain embodiments, the exponential-lognormal (EXP-LN) mixture requires $\sigma$ and F, along with a single log-mean for the high lognormal state ($\mu$) and a rate parameter for the low exponential state ($\lambda$). In some embodiments, the rate parameter relates to how quickly the lower distribution decays above zero copies per cell. In some embodiments, a rate parameter of $\lambda=1$ creates a distribution that has ~37% overlap with that of a high lognormal state of $\mu=0.5$ and $\sigma=0.225$ when F=50%. In other embodiments, $\lambda=3$ creates a distribution that has a ~6.3% overlap. In some embodiments, two distinct regulatory states can be modeled by restricting the simulations to rate parameters that cause negligible overlap with the high lognormal state ($\lambda>3$). In another embodiment, the different mixture models allow for simulation of stochastic-profiling data by summing the expression of 10 cells randomly sampled from the appropriate two-state distribution. As used herein, "stochastic-profiling" is intended to refer to methods that identify regulatory heterogeneities by repeatedly sampling small numbers of cells and profiling the samples for overall mRNA expression.

The term "sample," as used herein, is used in its broadest sense. A "biological sample," as used herein, includes, but is not limited to, any quantity of a substance from a living thing or formerly living thing. Such living things include, but are not limited to, humans, non-human primates, mice, rats, monkeys, dogs, rabbits and other animals. Such substances include, but are not limited to cells, blood (e.g., whole blood), plasma, serum, organs, and tissues.

In some embodiments, maximum-likelihood estimators for the LN-LN and EXP-LN mixtures are derived to infer the most-likely parameters from a collection of random 10-cell samples. In another embodiment, maximum-likelihood estimation requires a defined probability density function (pdf). In a further embodiment, the stochastic-sampling pdf is the convolution of 10 binomial choices drawn from the two underlying distributions in the mixture (See, for example, FIG. 3A and FIG. 3B). In a further embodiment, the pdf has a ≤11-modal shape where each mode corresponds to choosing 0 to 10 cells from the high regulatory state. In a further embodiment, the most-likely parameter combination is calculated by maximizing the likelihood function, yielding parameters with interval estimates that best explain the data (See, for example, FIG. 3A and FIG. 3B). For example, the maximum-likelihood inference of the regulatory state parameters is derived as in Example 2.

In some embodiments, the performance of the approach can be evaluated by using computational simulations of 10-cell samples with known distribution parameters. In a further embodiment, the minimum number of random samples needed to ensure accurate parameter estimation is identified. In a further embodiment, robust and accurate estimates can be obtained for all model parameters irrespective of the mixture type. For example, estimates can be obtained as described in Example 3. In some embodiments, 50-100 samples are the approximate number of data points required for effective maximum-likelihood inference of single transcripts.

In some embodiments, simulations are used to identify the parameter ranges where the disclosed maximum-likelihood inference makes accurate estimates of each regulatory state. In a further embodiment, one of $\mu_1$, $\mu_2$, $\sigma$, or F is perturbed in the LN-LN mixture while the other three parameters are fixed. In a further embodiment, 50 random 10-cell samples are simulated. In another embodiment, maximum-likelihood inference infers model parameters with negligible bias for a wide range of subpopulation log-means ($\mu_1$, and $\mu_2$). In another embodiment, altering the expression frequency (F) determines accuracy. In some embodiments, accuracy declines near F=50%, when the two subpopulations offset one another and disguise as a distribution with large $\sigma$. In some embodiments, performance declines only when the log-standard deviation ($\sigma$) is extremely high. In some embodiments, parameter estimates are accurate until $\sigma$ reaches ~0.8. In a further embodiment, none of the mixture parameters can be reliably inferred from higher-order moments of the 10-cell distributions. In a further embodiment, low F or high $\sigma$ correlates with a slight increase in skewness. For example, parameter ranges where the disclosed maximum-likelihood inference makes accurate estimates can be determined as in Example 3.

In certain embodiments, similar conclusions are reached for repeated simulations of the EXP-LN mixture. In a further embodiment, $\lambda$ and $\mu$ are large enough to prevent overlap of the two regulatory states. In another embodiment, the variance of inferred $\sigma$ was higher than in the LN-LN mixture.

In some embodiments, the method further comprises estimating the approximate confidence interval for the inferred parameters. In one embodiment, the approximate confidence interval is the 95% confidence interval. In some embodiments, the approximate confidence interval is estimated by numerically computing the inverse Hessian matrix of the negative log-likelihood function evaluated at the optimal parameter combination. For example, the approximate confidence interval can be estimated as described in Example 2.

In some embodiments, the disclosed method can be used to infer single-cell gene expression characteristics. In some embodiments, the disclosed method can be used to infer single-cell gene expression characteristics in cancer. For example, the disclosed maximum-likelihood estimation can be used to infer single-cell gene expression characteristics in an in vitro model of breast acinar morphogenesis. For example, single-cell gene expression characteristics can be inferred as described in Example 3. In some embodiments, the disclosed method can be used to examine the accuracy of maximum-likelihood inference with 10-cell samples. In one embodiment, the single-cell gene expression characteristics of individual genes can be inferred. For example, the expression characteristics of the detoxifying enzyme, SOD2, can be determined as described in Example 3. In some embodiments, at least 50 observations of 10-cell data are required to arrive at an accurate result.

In some embodiments, the coordinated single-cell gene programs are the product of an overarching regulatory heterogeneity characterized by a shared F. In a further embodiment, the expression frequency can be estimated confidently and with fewer samples by extending the maximum-likelihood inference to gene clusters with coordinated 10-cell fluctuations. As used herein, a "gene cluster" refers to a set of genes with a common expression pattern, for example similar sampling fluctuations. A common expression pattern of a gene cluster may indicate co-regulation of those genes.

In certain embodiments, each gene within a cluster is assigned its own $\mu_1$ and $\mu_2$ (or $\mu$ and $\lambda$ for the EXP-LN mixture) to account for gene-to-gene differences in expression level and detection sensitivity. In another embodiment, it is assumed that the genes within a cluster share a common F and $\sigma$ (or F, $\sigma_1$, and $\sigma_2$ in the relaxed LN-LN mixture), implying a shared mechanism of regulation. In a further embodiment, each mixture model of a cluster of g genes involves 2g+2 or 2g+3 parameters. For example, the expansion of the maximum-likelihood inference to a gene cluster is derived as in Example 2.

Figure 9:
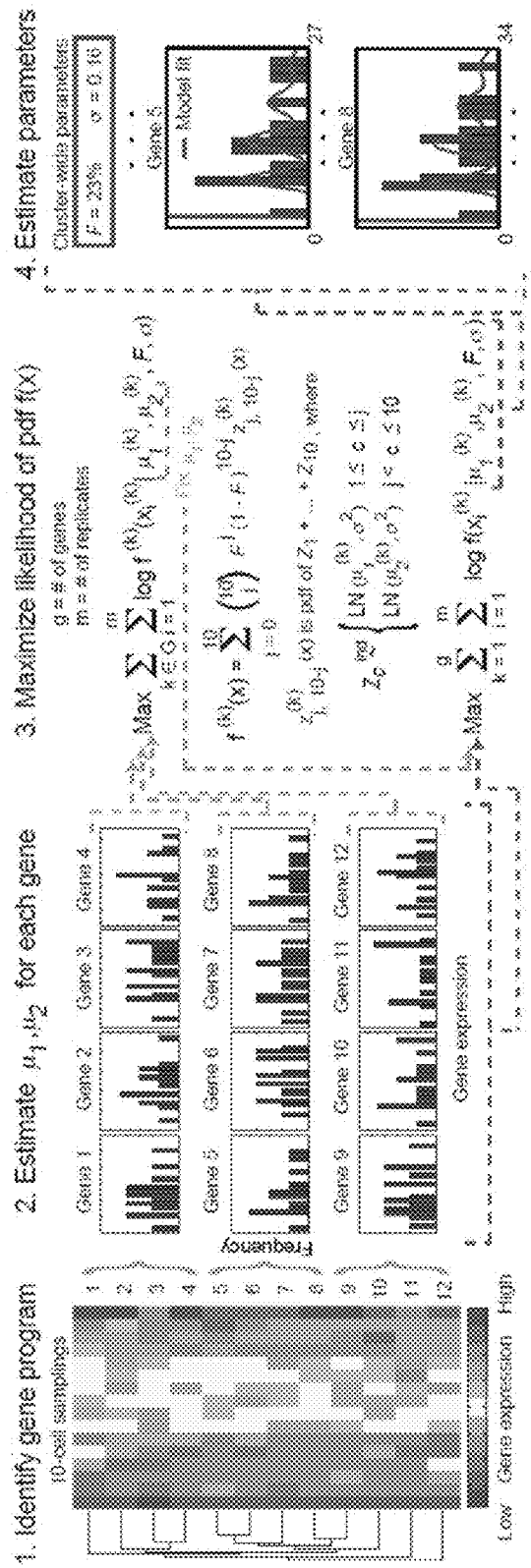
FIG. 9 shows the maximum-likelihood approach for gene clusters with coordinated 10-cell sampling.

In some embodiments, the cluster is broken down into smaller four-gene subgroups to infer log-means for each gene in the subgroup together with local estimates of F, $\sigma$, and $\lambda$ (FIG. 9). In some embodiments, the remaining parameters are globally inferred by re-maximizing the likelihood function for the entire gene cluster while retaining the local gene-specific estimates of $\mu_1$ and $\mu_2$ (LN-LN mixture) or $\mu$ (EXP-LN mixture) (FIG. 9). For example, expression characteristics of gene clusters can be inferred by the disclosed maximum-likelihood estimator as described in Example 4.

In certain embodiments, the disclosed extension of maximum-likelihood inference can infer expression characteristics of coexpression clusters. In a further embodiment, the clusters contain genes with coordinated expression fluctuations across samples. In one embodiment, the samples are derived from an in vitro model of mammary epithelial acinar morphogenesis. For example, the disclosed maximum-likelihood inference can be applied to infer expression characteristics as described in Example 4. In another embodiment, the patterns of fluctuation for each cluster are markedly different. In certain embodiments, the models predict the different expression frequencies according to the expression fluctuations of the samples. In some embodiments, the LN-LN mixture model is preferred over the EXP-LN or relaxed LN-LN mixtures. In another embodiment, all three models converge upon similar values for F.

In some embodiments, estimates of expression frequency are evaluated more broadly by selecting additional clusters from the same dataset for parameterization. In some embodiments, the clusters show distinct fluctuation patterns. In certain embodiments, maximum-likelihood inference provides information about the state distribution and expression frequency of any gene cluster identified by stochastic profiling to be heterogeneously regulated. In some embodiments, gene clusters from expression profiling data can be screened to identify unusual regulatory states.

In some embodiments, the predicted expression frequency of the high regulatory state of the cluster may be rare. In a further embodiment, the rare cluster is distinguished by its concordance with the relaxed LN-LN mixture compared with the alternative mixture models. For example, identification of an unusual regulatory state by the disclosed method may be done as disclosed in Examples 4 and 5. The term "rare," as used herein, describes an expression frequency of less than 20%, less than 15%, less than 10%, or less than 5%.

In certain embodiments, the disclosed method is more accurate than alternative methods that involve Bayesian statistics, nonnegative matrix factorization, or principal component analysis.

In certain embodiments, maximum-likelihood inference reconstructs the single-cell expression regulatory distribution without the need to measure single cells.

In some embodiments, the disclosure provides methods of inferring expression characteristics in a number of biological contexts. In a preferred embodiment, the method is applied to solid tissues, where single-cell dissociation and molecular profiling is especially problematic. In another embodiment, the regulatory heterogeneity is discovered in an unbiased manner.

In some embodiments, the present disclosure provides a method to enhance traditional stochastic profiling. In some embodiments, the method provides information about universal changes in gene expression. In some embodiments, the method quantifies the heterogeneous regulation of molecular states.

In some embodiments, the disclosed method deconvolves the distribution of single-cell regulatory states from stochastic gene expression profiling data via maximum-likelihood inference. In some embodiments, the method provides inferences that are more accurate than traditional stochastic profiling. In one embodiment, the method provides inferences that are more accurate than single-cell gene expression measurement.

In some embodiments, the disclosed method can be applied to the development of therapies.

Systems

Figure 22:
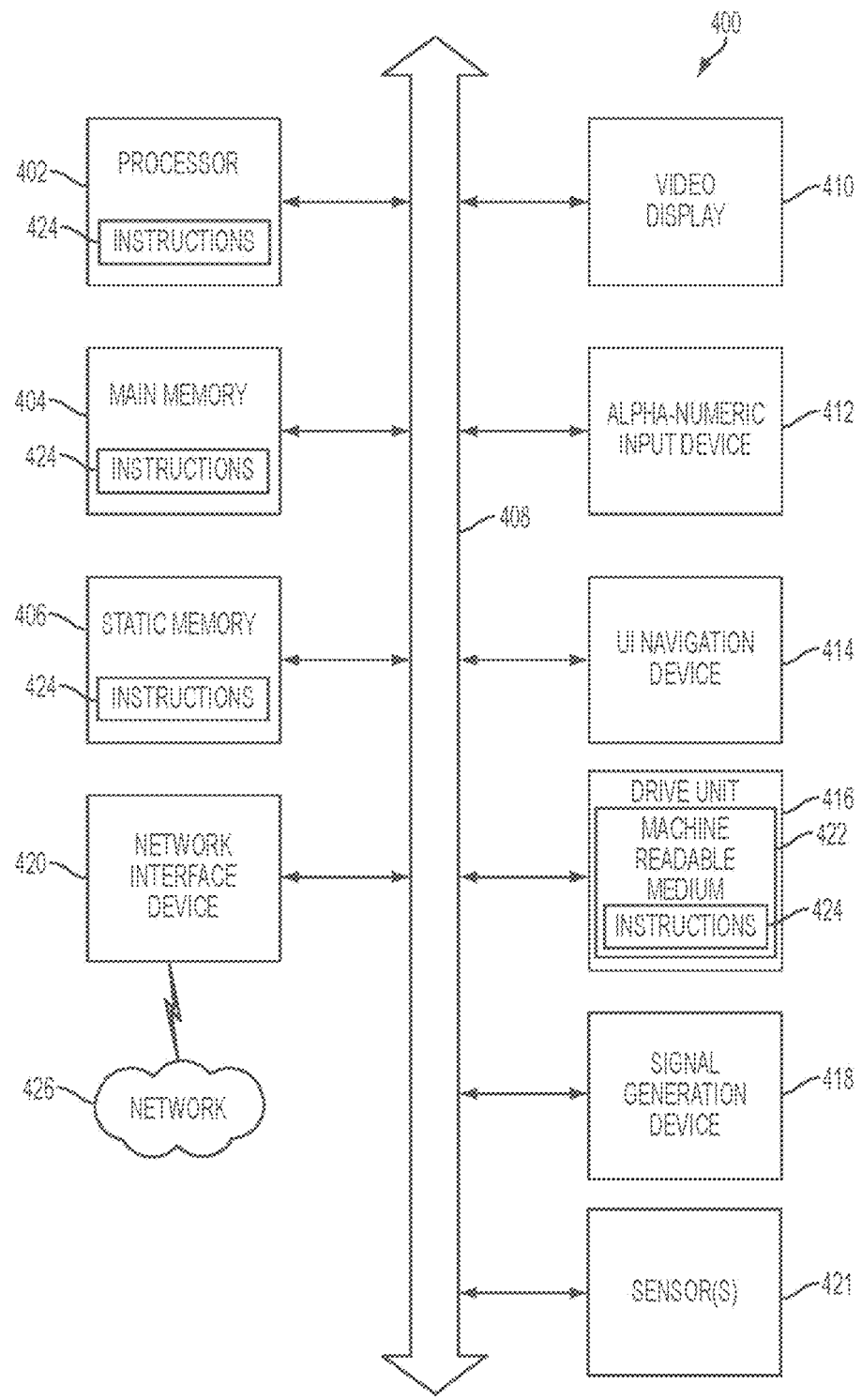
FIG. 22 is a block diagram illustrating an example of a machine upon which one or more aspects of embodiments of the present invention can be implemented.

In some embodiments, the disclosure further comprises a system for implementing the disclosed methods. FIG. 22 illustrates a block diagram of an example machine 400 upon which one or more embodiments (e.g., discussed methodologies) can be implemented (e.g., run). Examples of machine 400 can include logic, one or more components, circuits (e.g., modules), or mechanisms. Circuits are tangible or physical entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine-readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or more processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs)).

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and as static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 410, input device 417 and UI navigation device 414 can be a touch screen display.

The machine 400 can additionally include a storage device (e.g., drive unit) 416, a signal generation device 418 (e.g., a speaker), a network interface device 420, and one or more sensors 421, such as a global positioning system (OPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Figure 23:
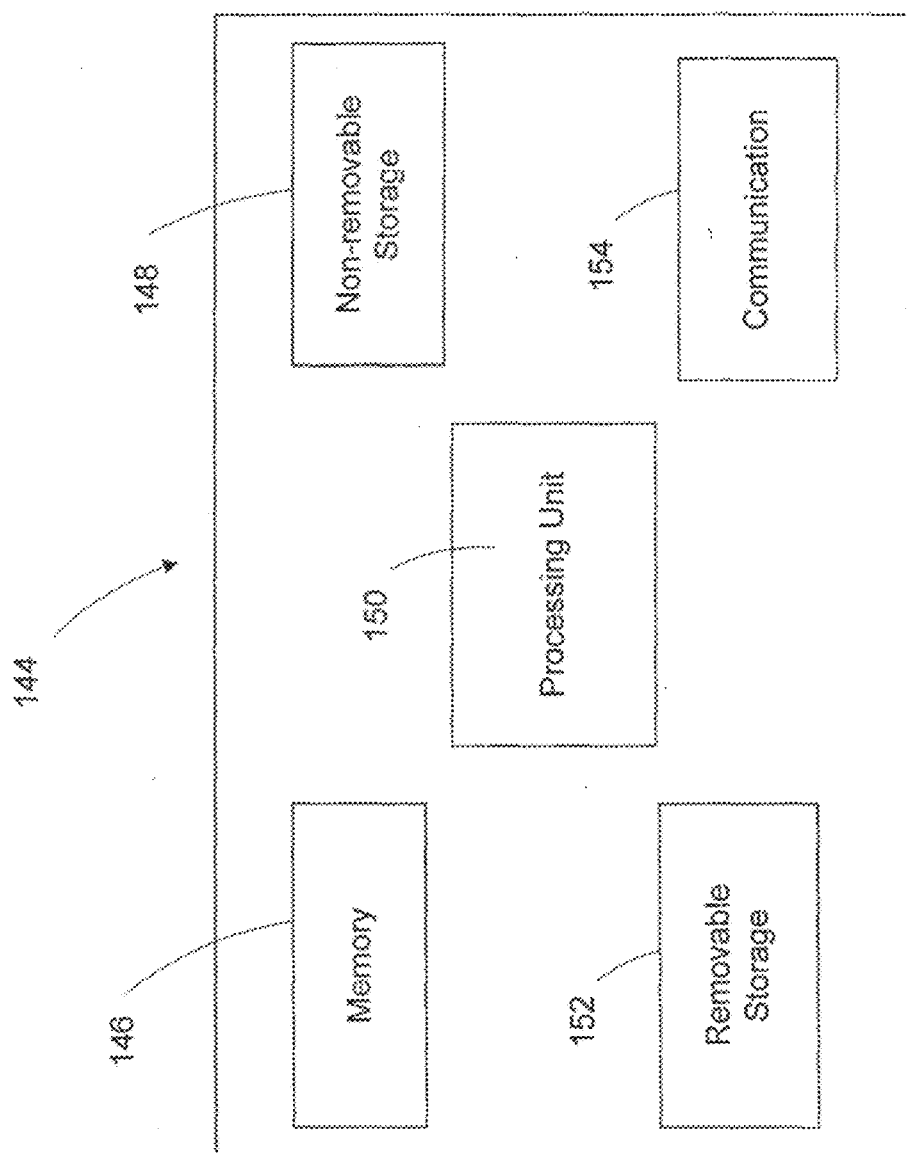
FIG. 23 illustrates a computing device upon which one or more aspects of embodiments of the present invention can be implemented.

Various embodiments or aspects of the invention, for example, can be implemented as software in a computing device, or alternatively, on hardware. An exemplary computing device in which an embodiment of the invention, or a portion thereof, can be implemented is schematically illustrated in FIG. 23. Although some aspects may be known, a brief explanation will be provided herein for the convenience of other readers.

Referring to FIG. 23, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is depicted in the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 24:
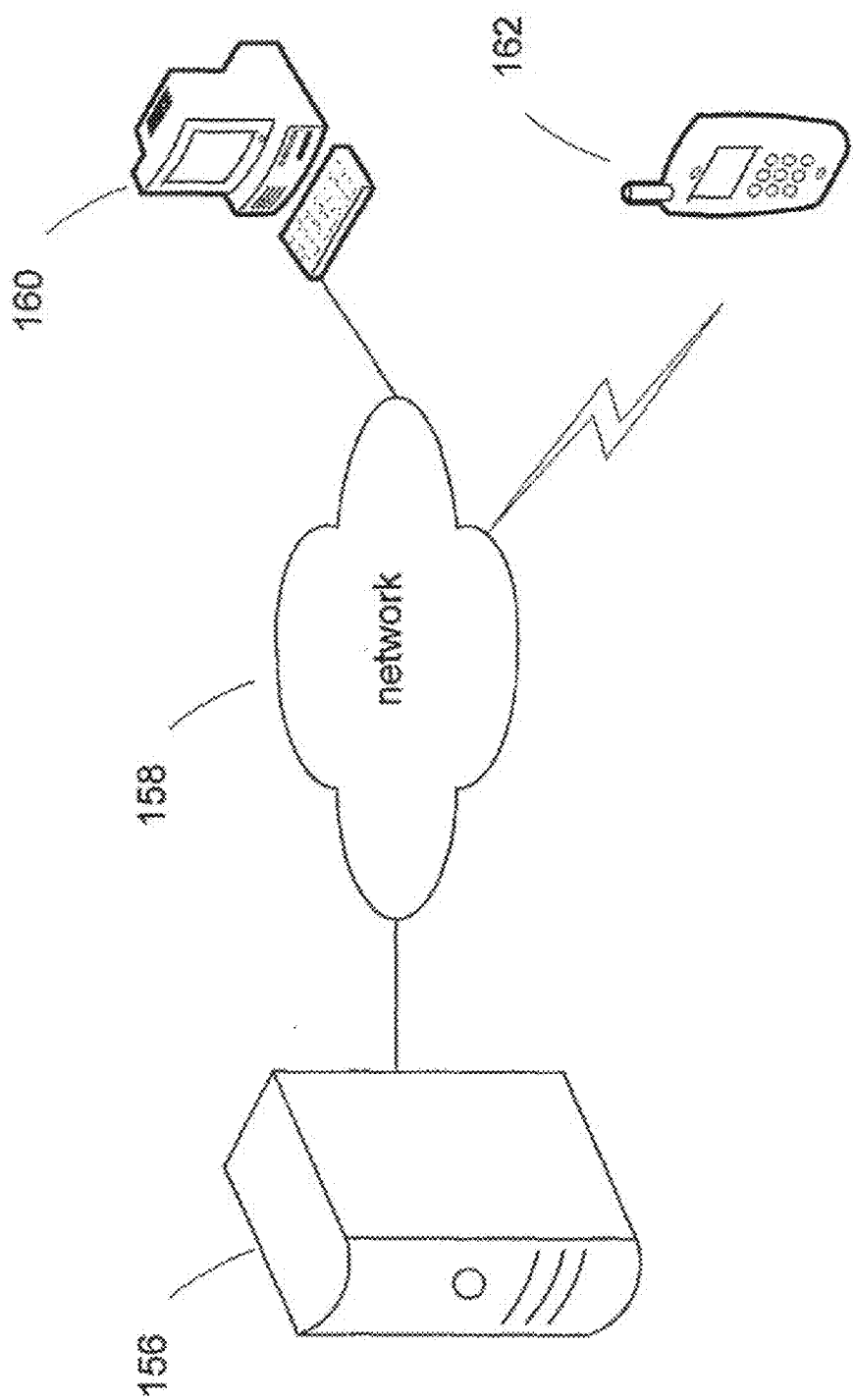
FIG. 24 illustrates a network system in which embodiments of the invention can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections, As a way of example. FIG. 24 illustrates a network system in which embodiments of the invention can be implemented, in this example, the network system comprises computer 156 (e.g. a network server), network connection means 158 (e.g. wired and/or wireless connections), computer terminal 160, and PDA (e.g. a smartphone) 162 (or other handheld or portable device, such as a cell phone, laptop computer, tablet computer, GPS receiver, mp3 player, handheld video player, pocket projector, etc. or handheld devices (or non portable devices) with combinations of such features). The embodiments of the invention can be implemented in any of the devices of the system. For example, execution of the instructions or other desired processing can be performed on the same computing device that is any of devices 156, 160, and 162. Alternatively, an embodiment of the invention can be performed on different computing devices of the network system. For example, certain desired or required processing or execution can be performed on one of the computing devices of the network (e.g., server 156), whereas other processing and execution of the instruction can be performed at another computing device (e.g., terminal 160) of the network system, or vice versa, in fact, certain processing or execution can be performed at one computing device (e.g., server 156); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA device, for example, accesses the network through computer terminal 160 (or an access point in an ad hoc network). For another example, software to be protected can be executed, encoded, or processed with one or more embodiments of the invention. The processed, encoded, or executed software can then be distributed to customers. The distribution can be in a form of storage media (e.g. disk) or electronic copy.

Disclosed embodiments may connect devices directly or indirectly with hardware that measures gene expression. In an embodiment, devices 156, 160, and/or 162 may connect to a gene expression measurement device (not shown) to receive digitized gene expression data. For example, devices 156, 160, and/or 162 may receive gene expression data from a microarray platform or an RNA sequencing platform, such as an Illumina BeadChip platform, an Affymetrix GeneChip® platform, an Agilent microarray platform, or an Illumina RNA-Seq platform. The connection between the gene expression measurement device and the computing device (e.g., device(s) 156, 160, and/or 162) may be over network 158 or using other connection protocols, such as USB or a serial connection. In an embodiment, devices 156, 160, and/or 162 may receive sequencing data from gene expression measurement hardware via a server. Gene expression measurement hardware may transmit gene expression data to a server for storing in a database. For example, gene expression measurement devices may transmit gene expression data to a centralized server, such as a server operated by a government agency (e.g., the National Center for Biotechnology information (NCBI) Gene Expression Omnibus (GEO)). Devices 156, 160, and/or 162 may receive gene expression data from a networked database. Specialized hardware, such as a supercomputer with high-throughput computational capacity or computer cluster, may perform disclosed processes to improve computational performance of processing digitized gene expression data.

An approach of the present invention systems and designs and optimization system and techniques may be based on the tools, programs and operating systems as discussed throughout this disclosure, such techniques can be applied to various hardware, tools, operating systems, virtual machine, PVM, or executable format.

Practice of an aspect of an embodiment (or embodiments) of the invention is presented herein for illustration only and should not be construed as limiting the invention in any way.

EXAMPLES

The following examples are intended to be illustrative and in no way limit the scope of the disclosure.

Example 1

Probability Models for Heterogeneous Transcriptional Regulation

A. Lognormal Distribution

Figure 2:
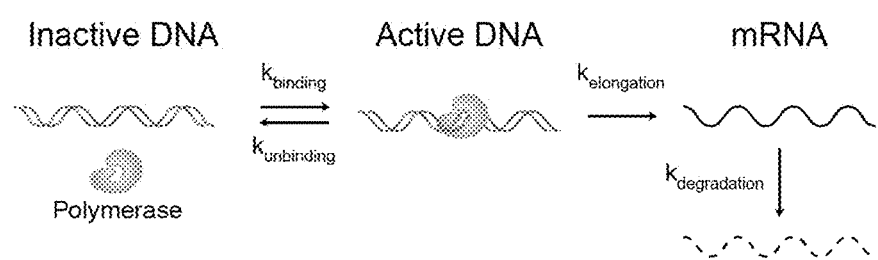
FIG. 2 shows a kinetic model of gene activation and mRNA expression.

To make single-cell inferences by the method of the present disclosure, simple probabilistic models of gene expression that were biologically accurate were developed. The method of the present disclosure considers genes that exhibit two distinct regulatory states in a population of cells. Within each state, the cell-to-cell variation of expression was originally described by a lognormal distribution according to measurements of high-copy transcripts in single mammalian cells (Bengtsson et al. (2005) *Genome research* 15(10):1388-1392; Warren et al. (2006) *Proc Natl Acad Sci U S A* 103(47):17807-17812). Whether there was a mechanistic foundation for using two lognormal subpopulations was investigated by examining a standard steady-state model of regulated gene expression (Peccoud & Ycart (1995) *Theor Popul Biol* 48(2):222-234; Raj et al. (2006) *PLoS Biol* 4(10):e309). In this model, transcript levels per cell are determined by the kinetics of polymerase binding-unbinding ($k_{binding}$), transcriptional elongation ($k_{elongation}$), and mRNA degradation ($k_{degradation}$) (FIG. 2). The relative magnitudes of the kinetic rate parameters together govern the steady-state distribution of transcripts in the population (Munsky et al. (2012) *Science* 336(6078):183-187), allowing different regulatory states to be simulated.

Distributions of transcripts per cell were generated under the steady-state approximation as previously described (Peccoud & Ycart (1995) *Theor Popul Biol* 48(2):222-234; Raj et al. (2006) *PLoS Biol* 4(10):e309). The basal lognormal regulatory state (FIG. 1A, blue) was defined with the following model parameters: $k_{binding}$=5, $k_{unbinding}$=10, $k_{elongation}$=50, and $k_{degradation}$=1. Basal regulatory states were perturbed by increasing $k_{binding}$ by 10-fold, decreasing $k_{degradation}$ by 3.3-fold, or both. Probabilities were compared with the lognormal test distributions by integrating over integer copy numbers to generate a representative observation set. Observations and distributions were compared with qqplot function in MATLAB (The Math Works).

For parameter sets where the probability of observing zero transcripts per cell was near zero, the lognormal distribution was a suitable approximation of basal expression (FIG. 1A, blue inset). Parameter sets yielding median expression levels as low as 20 copies per cell showed only minor skewness in quantile-quantile comparisons with a lognormal distribution (FIG. 1A, blue inset).

Starting with this basal distribution, a second regulatory state was simulated by increasing the rate the rate of polymerase binding, decreasing the rate of mRNA degradation, or both, as described above. The apparent rate of polymerase binding increases upon recruitment by transcription factors that are expressed or activated heterogeneously within a population of cells (Wernet et al. (2006) *Nature* 440(7081):174-180; Laslo et al. (2006) *Cell* 126(4):755-766). Conversely, mRNA stabilization occurs post-transcriptionally through dedicated signal transduction pathways activated by environmental stresses and proinflammatory stimuli (Gaestel (2006) *Nat Rev Mol Cell Biol* 7(2):120-130). Both mechanisms of gene up-regulation, respectively, led to right-shifted distributions that were lognormal (FIG. 1A, orange inset). These simulations indicated that lognormal random variables were appropriate for the regulated expression of mid- to high-abundance transcripts.

B. Exponential Distribution

Figure 1B:
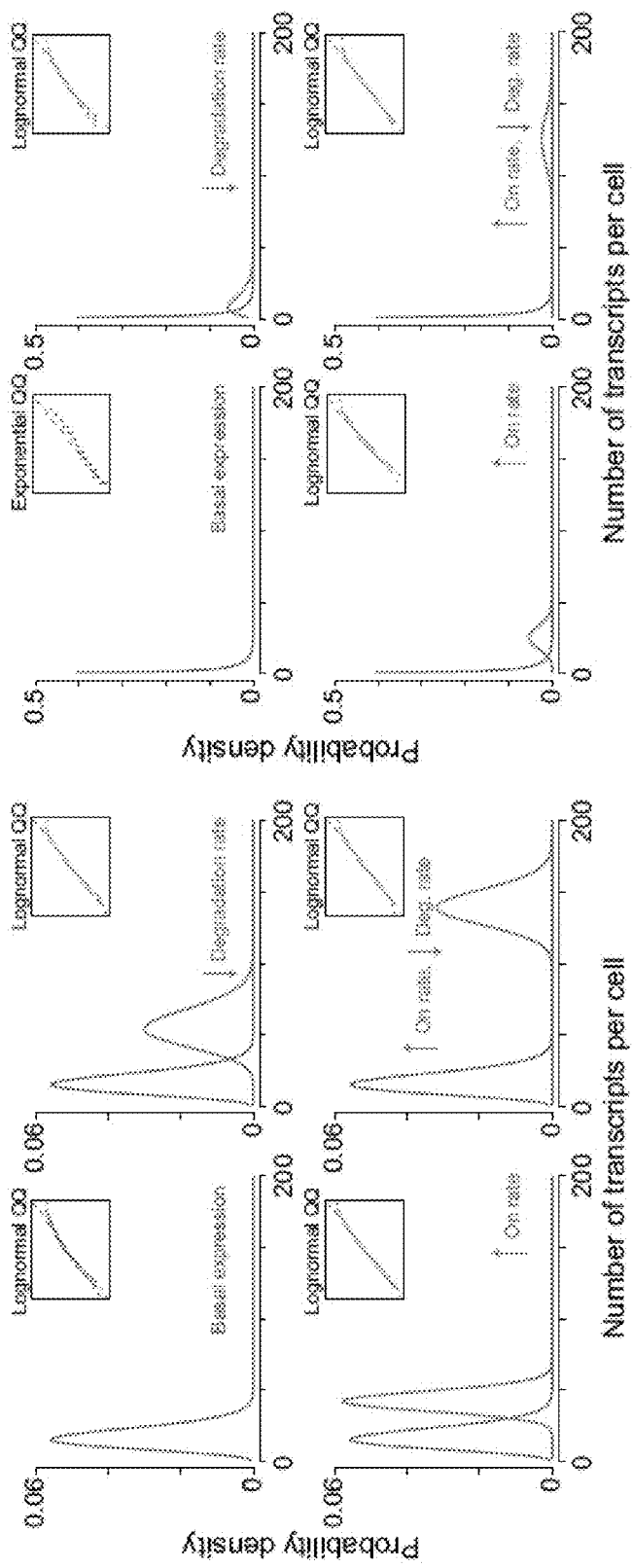
FIG. 1B shows probability densities for the number of transcripts per cell using a kinetic model having parameters that led to basal regulatory states (blue) with zero copies per cell.

The lognormal distribution has no support at zero copies of transcript, making it poor for capturing low-abundance genes that are completely silenced in some cells. The parameters of the basal state model were reconfigured to define a steady-state population where most cells would contain close to zero transcripts (FIG. 1B, blue). This regulated state was best captured by an exponential distribution (FIG. 1B, blue inset) and referred to as the exponential regulatory state.

The exponential regulatory state was defined with the following model parameters: $k_{binding}$=0.5, $k_{unbinding}$=10, $k_{elongation}$=50, and $k_{degradation}$=1. Basal regulatory states were perturbed by increasing $k_{binding}$ by 20-fold, decreasing $k_{degradation}$ by 5-fold, or both. Probabilities were compared with the lognormal test distributions by integrating over integer copy numbers to generate a representative observation set. Observations and distributions were compared with qqplot function in MATLAB (The Math Works).

When the kinetic parameters of a basal exponential state were perturbed as described as above to create a second right-shifted state (FIG. 1B, orange), the resulting distributions were lognormal (FIG. 1B, orange inset). Together, the basic mechanisms of gene expression lead to steady-state distributions could be described by probability models that are relatively simple. The results from the gene-expression model suggested that single-cell regulatory heterogeneities could be depicted as a mixture of two lognormal states or as a mixture of an exponential state and a lognormal state.

Example 2

Deconvolution of Random 10-cell Averages by Maximum-likelihood Inference

Each of the single-cell regulatory heterogeneities depicted as either a mixture of two lognormal states or as a mixture of an exponential state and a lognormal state, gives rise to a probability distribution characterized by four key parameters. The LN-LN mixture requires the log-mean expression of the basal regulatory state ($\mu_2$), the log-mean expression of the induced regulatory state ($\mu_1$), the log-standard deviation (SD) for biological noise ($\sigma$), and the probability of drawing a single cell from the high regulatory state is described as the expression frequency (F) (FIG. 3A, step 1). The weight of each subpopulation is defined by the integrated single-cell expression distribution of the subpopulation ($\varphi_1$ and $\varphi_2$), and $$F = \frac{\phi 1}{\phi 1 + \phi 2}.$$

For simulations, the two lognormal states are assumed to share a common but in practice it was tested whether the inferences are improved when each lognormal state is allowed its own noise parameter ("relaxed LN-LN" mixture). Thus, an LN-LN gene that is expressed at an approximately eightfold higher level in 20% of the population with a coefficient of variation (CV) of ~50% is captured by $\mu_1 - \mu_2 = 2$, F=20%, and $\sigma$=0.48.

The exponential-lognormal (EXP-LN) mixture also requires $\sigma$ and F, along with a single log-mean for the high lognormal state ($\mu$) and a rate parameter for the low exponential state ($\lambda$) (FIG. 3B, step 1). The rate parameter relates to how quickly the lower distribution decays above zero copies per cell. For example, a rate parameter of $\lambda=1$ creates a distribution that has ~37% overlap with that of a high lognormal state of $\mu=0.5$ and $\sigma=0.225$, whereas $\lambda=3$ causes only a ~6.3% overlap. Two distinct regulatory states were modeled by restricting the simulations to rate parameters that caused negligible overlap with the high lognormal state ($\lambda>3$). Together, the different mixture models enable simulation of stochastic-profiling data by summing the expression of 10 cells randomly sampled from the appropriate two-state distribution (FIG. 3A, step 2, and FIG. 3B, step 2).

To infer the most-likely parameters from a collection of random 10-cell samples, the maximum-likelihood estimators for the LN-LN and EXP-LN mixtures were derived. Maximum-likelihood estimation requires a defined probability density function (pdf). The stochastic-sampling pdf is the convolution of 10 binomial choices drawn from the two underlying distributions in the mixture (FIG. 3A, step 3, and FIG. 3B, step 3). The pdf has a $\leq 11$-modal shape were each mode corresponds to choosing 0-10 cells from the high regulatory state. The most-likely parameter combination is calculated by maximizing the likelihood function, yielding parameters with interval estimates that best explained the data (FIG. 3A, step 4, and FIG. 3B, step 4). By performing the maximum-likelihood estimation, the stochastic profiling data could be "inverted" to infer single-cell characteristics from 10-cell samples.

A. Derivation of the Maximum Likelihood Estimator

The panel of maximum-likelihood estimators was derived by assuming a mixed population of cells occupying one of two regulatory states. The basal regulatory state expresses a transcript (g) at a low level with 1) log-mean $\mu_2^{(g)}$ and log-SD $\sigma$ for the LN-LN model, 2) log-mean $\mu_2^{(g)}$ and log-SD $\sigma_2$ for the relaxed LN-LN model, or 3) mean and standard deviation $(\lambda^{(g)})^{-1}$ for the EX-LN model. The induced regulatory state expresses the transcript at a higher level with 1) log-mean $\mu_1^{(g)}$ and log-SD $\sigma$ for the LN-LN model, 2) log-mean $\mu_1^{(g)}$ and log-SD $\sigma_1$ for the relaxed LN-LN model, or 3) log-mean $\mu^{(g)}$ and log-SD $\sigma$ for the EXP-LN model. In all mixture models, the probability of drawing a single cell from the high regulatory state is characterized by the parameter F.

According to the two-state model, the single-cell expression for transcript g follows the pdf:

$$f_{mixture}^{(g)} = F \cdot f_1^{(g)} + (1-F) \cdot f_2^{(g)} \qquad (1)$$

where $f_2^{(g)}$ and $f_1^{(g)}$ for the LN-LN mixture model are defined as:

$$f_v^{(g),LN-LN}(x) = \frac{1}{\sqrt{2\pi}\,\sigma x} \cdot \exp\left\{-\frac{[\log(x)-\mu_v^{(g)}]^2}{2\sigma^2}\right\} \qquad (2)$$

for $x > 0$ and $v \in \{1, 2\}$, $f_2^{(g)}$ and $f_1^{(g)}$ for the relaxed LN-LN mixture model are defined as:

$$f_v^{(g),rLN-LN}(x) = \frac{1}{\sqrt{2\pi}\,\sigma_v x} \cdot \exp\left\{-\frac{[\log(x)-\mu_v^{(g)}]^2}{2\sigma_v^2}\right\} \qquad (3)$$

for $x > 0$ and $v \in \{1, 2\}$, and $f_2^{(g)}$ and $f_1^{(g)}$ for the EXP-LN mixture model are defined as:

$$f_2^{(g),EXP-LN}(x) = \lambda^{(g)} \cdot \exp(-\lambda^{(g)} \cdot x) \quad \text{for } x \geq 0 \qquad (4)$$

$$f_1^{(g),EXP-LN}(x) = \frac{1}{\sqrt{2\pi}\,\sigma x} \cdot \exp\left\{-\frac{[\log(x)-\mu^{(g)}]^2}{2\sigma^2}\right\}$$

for $x > 0$.

The $i^{th}$ random sample of transcript g, $Y_i^{(g)}$, is the sum of n independent single-cell expression measurements (here, n=10):

$$Y_i^{(g)} = \sum_{j=1}^{n} X_{ij}^{(g)}, \qquad (5)$$

where $X_{ij}^{(g)}$ is the expression of transcript g in the $j^{th}$ cell of the $i^{th}$ random sample. Together, the random sample $Y_i^{(g)}$ describing the n-cell mixture has the pdf:

$$f_n^{LN-LN}(y \mid F, \mu_1^{(g)}, \mu_2^{(g)}, \sigma) = \sum_{j=0}^{n} \binom{n}{j} F^j (1-F)^{n-j} f_{(j,n-j)}^{(g),LN-LN}(y), \qquad (6)$$

the relaxed LN-LN mixture has the pdf:

$$f_n^{rLN-LN}(y \mid F, \mu_1^{(g)}, \mu_2^{(g)}, \sigma_1, \sigma_2) = \qquad (7)$$

$$\sum_{j=0}^{n} \binom{n}{j} F^j (1-F)^{n-j} f_{(j,n-j)}^{(g),rLN-LN}(y),$$

and the EXP-LN mixture has the pdf:

$$f_n^{EXP-LN}(y \mid F, \mu^{(g)}, \lambda^{(g)}, \sigma) = \sum_{j=0}^{n} \binom{n}{j} F^j (1-F)^{n-j} f_{(j,n-j)}^{(g),EXP-LN}(y). \qquad (8)$$

$$\binom{n}{j} F^j (1-F)^{n-j}$$

represents the binomial selection of cells from the basal or induced regulatory states with probabilities F and 1−F, respectively. $f_{(j, n-j)}^{(g)}$ is the density of a sum $Z_1 + \ldots + Z_n$ of independent random variables representing the n-cell draw from the following mixture models:

$$Z_c^{LN-LN} = \begin{cases} LN(\mu_1^{(g)}, \sigma^2) & \text{if } 1 \leq c \leq j \\ LN(\mu_2^{(g)}, \sigma^2) & \text{if } j < c \leq n \end{cases} \text{(LN-LN mixture),} \qquad (9)$$

$$Z_c^{rLN-LN} = \begin{cases} LN(\mu_1^{(g)}, \sigma_1^2) & \text{if } 1 \leq c \leq j \\ LN(\mu_2^{(g)}, \sigma_2^2) & \text{if } j < c \leq n \end{cases} \text{(relaxed LN-LN mixture),} \qquad (10)$$

-continued $$Z_c^{EXP-LN} = \begin{cases} LN(\mu^{(g)}, \sigma^2) & \text{if } 1 \le c \le j \\ EXP(\lambda^{(g)}) & \text{if } j < c \le n \end{cases} \quad \text{(EXP-LN mixture).} \quad (11)$$

The pdf for the sum of lognormally distributed random variables was approximated as previously described (Slack et al. (2008) *Proc Natl Acad Sci U S A* 105(49):19306-19311) and applied to the LN-LN and relaxed LN-LN mixture models. The sum of independent, exponentially distributed random variables follows an Erlang distribution (Raj et al. (2010) *Nature* 463(7283):913-918). The pdf for the EXP-LN mixture model is the convolution of a lognormal and an Erlang density, whose integral was solved numerically.

When expanded to a cluster of m transcripts, the log-likelihood function for the model parameters given k random n-cell samples is:

$$l^{LN-LN}(F, \underline{\mu_1}, \underline{\mu_2}, \sigma) = \sum_{g=1}^{m}\sum_{i=1}^{k} \log[f_n^{LN-LN}(y_i^{(g)} \mid F, \mu_1^{(g)}, \mu_2^{(g)}, \sigma)] \quad (12)$$

(LN-LN mixture), $$l^{rLN-LN}(F, \underline{\mu_1}, \underline{\mu_2}, \sigma_1, \sigma_2) = \quad (13)$$
$$\sum_{g=1}^{m}\sum_{i=1}^{k} \log[f_n^{rLN-LN}(y_i^{(g)} \mid F, \mu_1^{(g)}, \mu_2^{(g)}, \sigma_1, \sigma_2)]$$

(relaxed LN-LN mixture), $$l^{EXP-LN}(F, \underline{\mu}, \underline{\lambda}, \sigma) = \sum_{g=1}^{m}\sum_{i=1}^{k} \log[f_n^{EXP-LN}(y_i^{(g)} \mid F, \mu^{(g)}, \lambda^{(g)}, \sigma)] \quad (14)$$

(EXP-LN mixture).

where $\underline{\mu_1}$, $\underline{\mu_2}$, $\underline{\mu}$, and $\underline{\lambda}$ are vectors containing the transcript-specific log-means (or inverse means for $\underline{\lambda}$ in EXP-LN mixture) for the two regulatory states: $\underline{\mu_1}=(\mu_1^{(1)}, \ldots, \mu_1^{(m)})$, $\underline{\mu_2}=(\mu_2^{(1)}, \ldots, \mu_2^{(m)})$, $\underline{\mu}=(\mu^{(1)}, \ldots, \mu^{(m)})$, and $\underline{\lambda}=(\lambda^{(1)}, \ldots, \lambda^{(m)})$. The log-likelihood functions assume that the expression levels of each transcript are independent as defined by the specific mixture model and F.

B. Maximum-Likelihood Parameter Estimation and Model Selection.

The derived log-likelihood functions in Equations 12-14, described above, are maximized by the most likely combination of parameters for the data $Y_i^{(g)}$. To estimate the parameters for the LN-LN mixtures, it was required that $\mu_1^{(1)} > \mu_2^{(1)}$. This constraint ensured identifiability because $l(F, \underline{\mu_1}, \underline{\mu_2}, \sigma) = l(1-F, \underline{\mu_2}, \underline{\mu_1}, \sigma)$. F was also transformed with the logit function and $\underline{\lambda}$ and $\sigma$ with the logarithm function to enable the use of faster, unconstrained optimization algorithms.

Because the log-likelihood function was multimodal, it precluded the straightforward use of gradient-based approaches to find globally optimal parameter combinations. The high-dimensional nonconvex global optimization problem was solved by combining genetic and simplex algorithms. First, the log-likelihood function was computed at randomly drawn parameter combinations to identify high-likelihood regions in parameter space at computationally low cost. In the regions of highest log likelihood, the Nelder-Mead algorithm (Nelder & Meade (1965) *Comput J* 7(4):308-313) was then used to identify local maxima of the likelihood function. The global optimum was further localized by repeating a random search of parameter space around the optimum identified by the Nelder-Mead algorithm. The resulting high-likelihood regions were used to seed another Nelder-Mead optimization. The iterations of random search and Nelder-Mead optimization continued until convergence.

Figure 11:
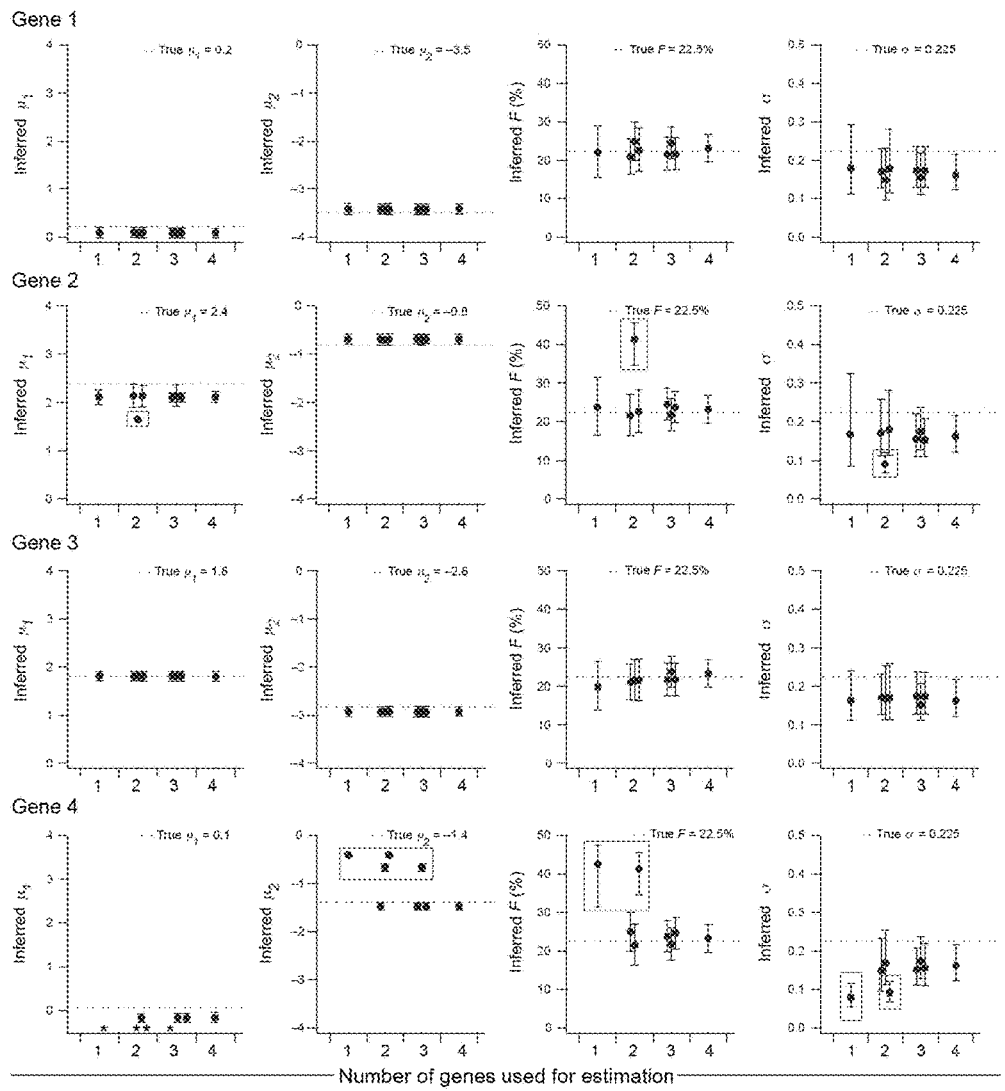
FIG. 11 shows that parameter estimation with limited samples is improved by evaluating coexpression clusters.

For estimating model parameters from transcriptional clusters, smaller subgroups of the cluster of interest were first considered. The best balance of computational time and stability of the resulting parameter estimates was achieved with four-gene subgroups (FIG. 11, see Example 4). The log likelihood of each subgroup was optimized by the algorithm described above to identify the most-likely parameters for the transcripts in the subgroup. Based on the subgroup estimate, we kept fixed $\underline{\mu_1}$ and $\underline{\mu_2}$ (for the LN-LN and relaxed LN-LN models) or $\underline{\mu}$ (for the EXP-LN model) and globally inferred F and $\sigma$ (or F, $\sigma_1$, and $\sigma_2$ for the relaxed LN-LN model, or $\underline{\lambda}$, F, and $\sigma$ for the EXP-LN model) by using the optimization algorithm described above. To confirm that the global optimum for each model had been identified, a constrained optimization was pursued in parallel, which required that the two regulatory states be sufficiently distinct from each other. Specifically, the density of the high regulatory state was constrained to be greater than the low regulatory state in the domain between the mode of the high state and the largest observation in the dataset. The likelihoods of the constrained and unconstrained optimizations were compared, and the higher likelihood inference was selected as the best parameterization for that mixture model. Last, the three mixture models were compared according to their BIC score, BIC being defined by the following equation:

$$BIC = -2l(\hat{\theta}) + c\log(mk)$$

where $\hat{\theta}$ is the vector of inferred parameters, c is the number of inferred parameters in the model, m is the number of transcripts in the cluster, and k is the number of n-cell random samples for each transcript. The best model predicted two distinct regulatory states with the lowest BIC score (see Example 3).

Approximate 95% confidence intervals (CI) were estimated by numerically computing the inverse Hessian matrix of the negative tog-likelihood function evaluated at the optimal parameter combination. Each $i^{th}$ diagonal element $(d_i)$ of this matrix leads to the confidence in the $i^{th}$ inferred parameter $\hat{\theta}_i$ as follows:

$$95\% \; CI_i = \hat{\theta}_i \pm 1.96\sqrt{d_i}.$$

Example 3

Theoretical Validation of Maximum-likelihood Inference

A. Validation with Simulated Data

The performance of the maximum-likelihood inference was evaluated using computational simulations of 10-cell samples with known distribution parameters. Simulated 10-cell expression profiles were generated in MATLAB with the statistics toolbox or in R. The LN-LN model assumes a binomial distribution for the two regulatory states and a lognormal distribution of the transcripts within each state. For a random n-cell sampling (here n=10), the number of cells drawn from the high regulatory state (h) was specified by a binomial distribution with parameters n and F. Next, h expression measurements were randomly drawn from a lognormal distribution with log-mean $\mu_1$ and log-SD $\sigma$. The remaining n–h expression measurements were also drawn from a lognormal distribution with log-mean $\mu_2$ and log-SD $\sigma$. The sum of n measurements constituted one stochastic n-cell sample. In the EXP-LN model, transcripts from the basal regulatory state were drawn from an exponential distribution with rate parameter $\lambda$. This procedure was repeated for the indicated number of random samples.

First, it was important to identify the minimum number of random samples needed to ensure accurate parameter estimation. Given. hundreds to thousands of samples, robust and accurate estimates were obtained for all model parameters irrespective of the mixture type (FIG. 6A and FIG. 6B). Conversely, with very few samples (~20 or fewer), the convolved distributions were incompletely populated and the resulting estimates were highly uncertain and sometimes inaccurate for the LN-LN and EXP-LN mixtures. The transition between the two regimes occurred at 50-100 samples, which was defined as the approximate number of data points required for effective maximum-likelihood inference of single transcripts.

Figures 4A, 4B, 4C, 4D:
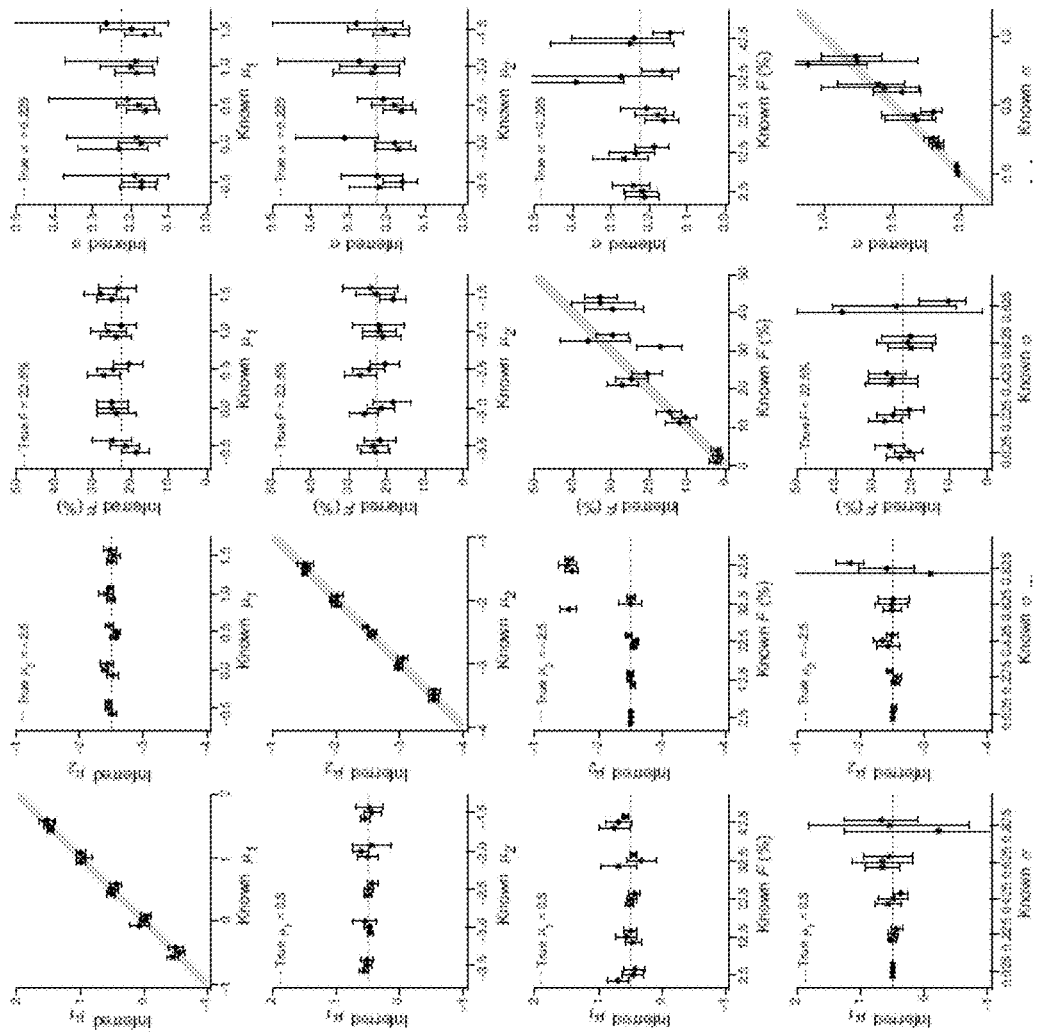
FIG. 4A shows accurate predictions of single-cell parameters from simulated 10-cell samples. 10-cell expression data was simulated using different values of $\mu_1$ and the remaining three model parameters were kept fixed.
FIG. 4B shows accurate predictions of single-cell parameters from simulated 10-cell samples. 10-cell expression data was simulated using different values of $\mu_2$ and the remaining three model parameters were kept fixed.
FIG. 4C shows accurate predictions of single-cell parameters from simulated 10-cell samples. 10-cell expression data was simulated using different values of F and the remaining three model parameters were kept fixed.
FIG. 4D shows accurate predictions of single-cell parameters from simulated 10-cell samples. 10-cell expression data was simulated using different values of $\sigma$ and the remaining three model parameters were kept fixed.
Figure 7A:
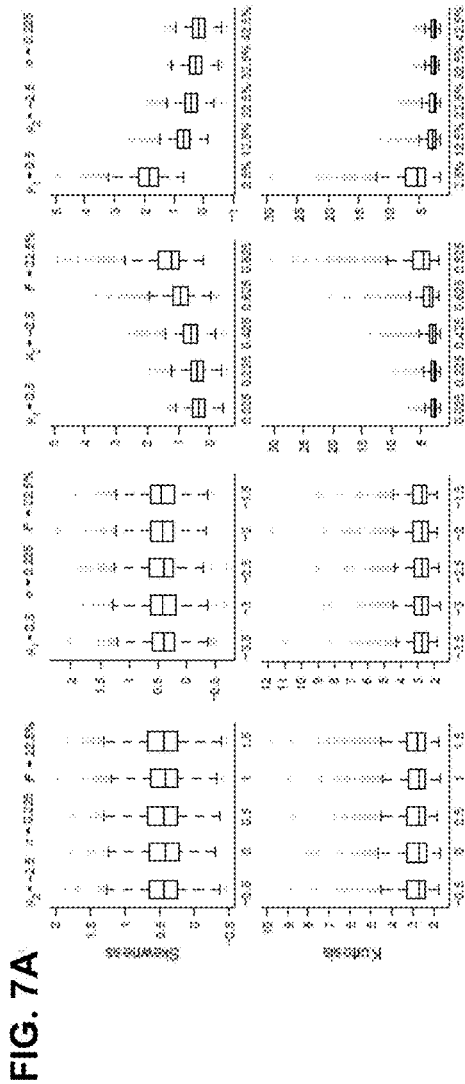
FIG. 7A shows that skewness and kurtosis are not strongly predictive of subpopulation parameters. Stochastic profiles were computationally simulated with three fixed parameters and one varying parameter (x-axis) for the LN-LN mixture with 50 samples.
Figure 7B:
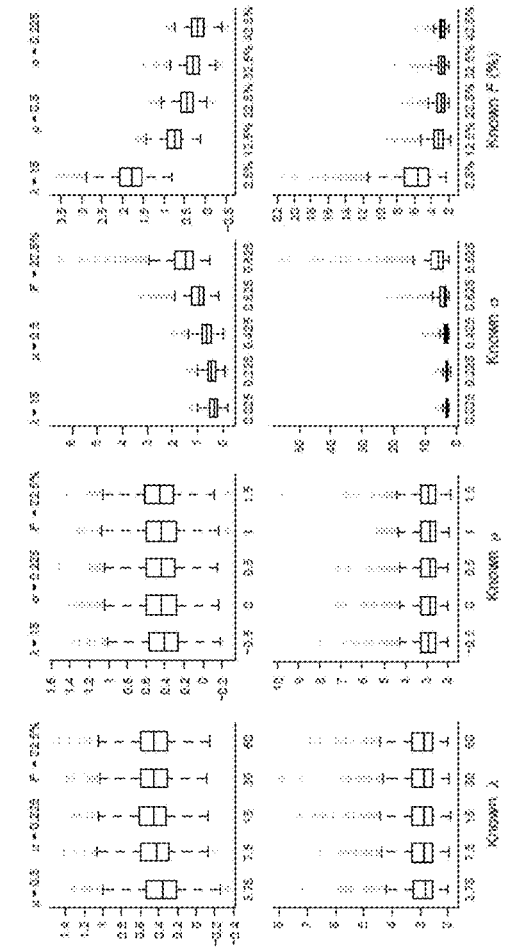
FIG. 7B shows that skewness and kurtosis are not strongly predictive of subpopulation parameters. Stochastic profiles were computationally simulated with three fixed parameters and one varying parameter (x-axis) for the EXP-LN mixture with 100 samples (B).

Next, simulations were used to identify the parameter ranges where maximum-likelihood inference makes accurate estimates of each regulatory state. Start with the LN-LN mixture, $\mu_1$, $\mu_2$, $\sigma$, or F were perturbed individually while keeping the other three parameters fixed and simulated 50 random 10-cell samples, For a wide range of subpopulation log-means ($\mu_1$ and $\mu_2$), maximum-likelihood inference accurately inferred model parameters with negligible bias (FIG. 4A and FIG. 4B). Good performance was also observed when altering the expression frequency (F). Accuracy declined near F=50%, when the two subpopulations offset one another and disguise as a distribution with large $\sigma$ (FIG. 4C). Nevertheless, the estimation procedure still accurately and confidently captured ~70% of the total parameter space (F=0-35% over the range of 0-50%). For the log-SD ($\sigma$), performance declined only when this parameter was extremely high (FIG. 4D) Parameter estimates were accurate until $\sigma$ reached ~0.8, corresponding to a ~95% CV that is higher than nearly all genes examined thus far (Newman et al. (2006) *Nature* 441(7095):840-846; Bar-Even et al. (2006) *Nat Genet* 38(6):636-643). None of the mixture parameters could he reliably inferred from higher-order moments of the 10-cell distributions, although low F or high $\sigma$ correlated with a slight increase in skewness (FIG. 7). These results indicated that maximum-likelihood inferences could extract parameters that were otherwise inaccessible by descriptive statistics.

Figures 8A, 8B, 8C, 8D:
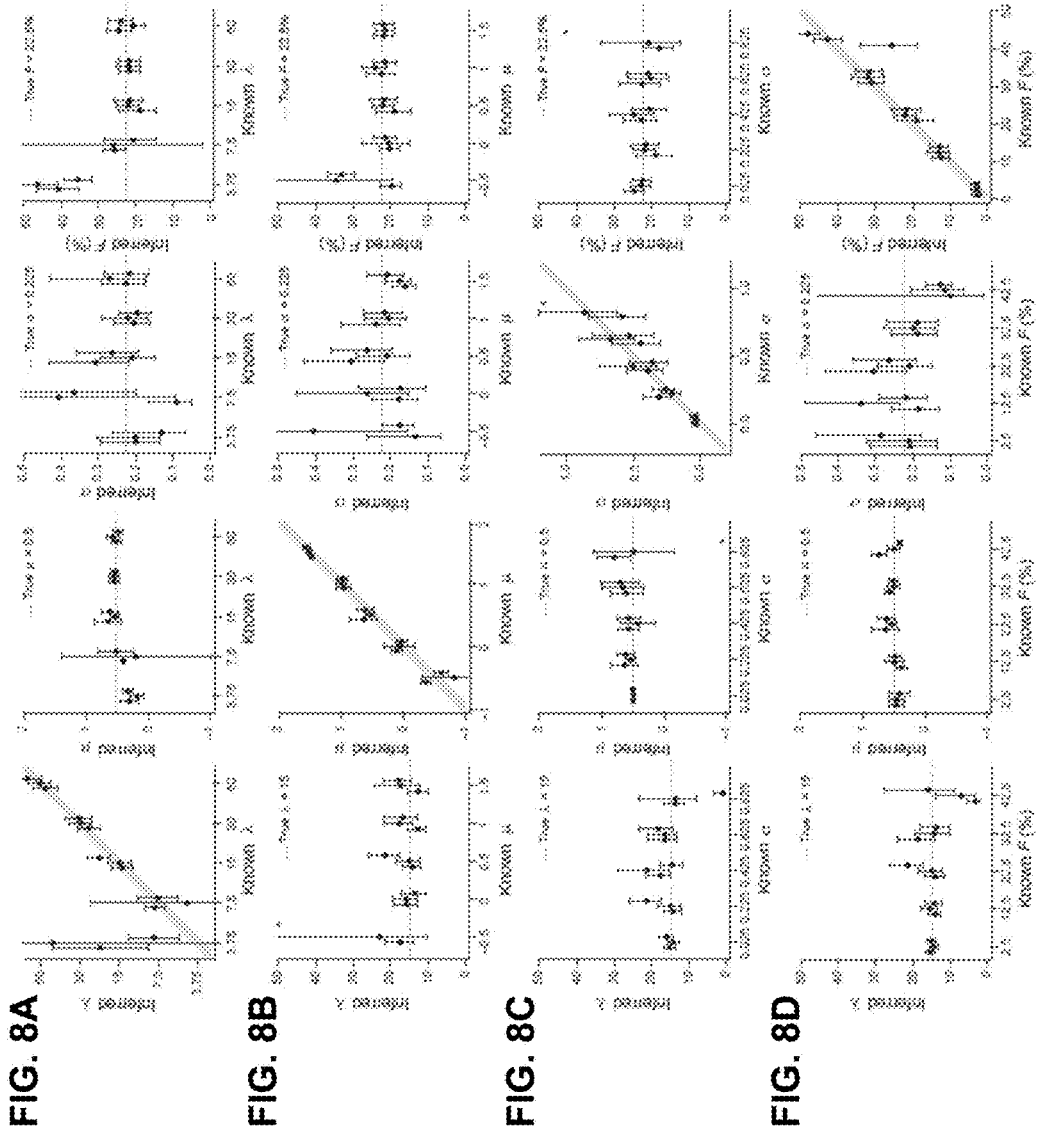
FIG. 8A shows the accurate prediction of single-cell parameters from simulated 10-cell samples of an EXP-LN mixture of regulatory states. 10-cell expression data were simulated using different values of $\lambda$ then estimated by maximum likelihood.
FIG. 8B shows the accurate prediction of single-cell parameters from simulated 10-cell samples of an EXP-LN mixture of regulatory states. 10-cell expression data were simulated using different values of $\mu$ then estimated by maximum likelihood.
FIG. 8C shows the accurate prediction of single-cell parameters from simulated 10-cell samples of an EXP-LN mixture of regulatory states. 10-cell expression data were simulated using different values of $\sigma$ then estimated by maximum likelihood.
FIG. 8D shows the accurate prediction of single-cell parameters from simulated 10-cell samples of an EXP-LN mixture of regulatory states. 10-cell expression data were simulated using different values of F then estimated by maximum likelihood.

The simulations were repeated for the EXP-LN mixture and the conclusions arrived at were very similar to the LN-LN mixture. As long as $\lambda$ and $\mu$ were large enough to prevent overlap of the two regulatory states, the parameter estimates were accurate, although the variance of inferred $\sigma$ was somewhat higher than in the LN-LN mixture (FIG. 8). Together, these simulations suggested that maximum-likelihood inference is able to deconvolve a wide range of regulatory heterogeneities from 10-cell samples.

B. Maximum-Likelihood Inferences of SOD2 Expression in vitro

The accuracy of maximum-likelihood inference with real 10-cell samples was examined using expression of the detoxifying enzyme superoxide dismutase 2 (SOD2) during breast-epithelial acinar morphogenesis. A culture model in which immortalized human breast epithelial cells are grown as single-cell clones in reconstituted basement-membrane extracellular matrix (ECM) to form 3D organotypic spheroids was used (Debnath et al. (2003) *Methods* 30(3):256-268; Debnath & Brrugge (2005) *Nat Rev Cancer* 5(9):675-688). The MCF10A-5E clone was maintained as previously described (Janes et al. (2010) *Nat Methods* 7(4):311-317).

Figure 5A:
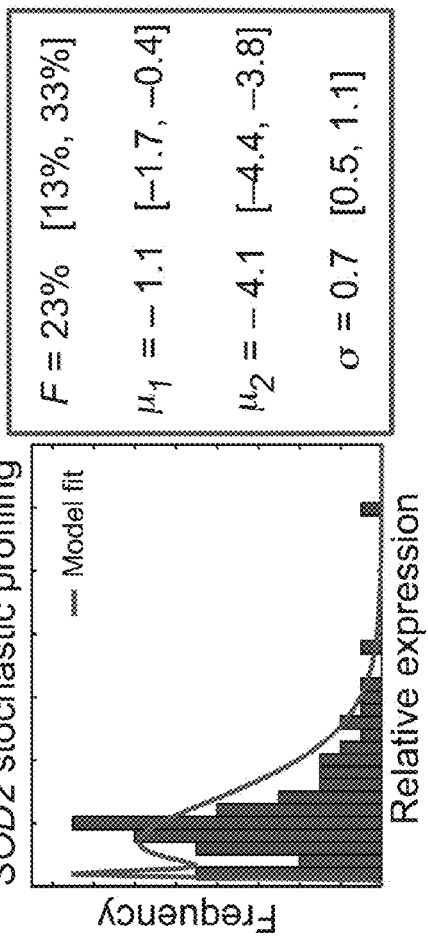
FIG. 5A shows the distribution of 81 ten-cell qPCR measurements of SOD2 in outer ECM-attached epithelial cells and estimated subpopulation distribution (red line).

Earlier stochastic-profiling studies of developing spheroids had suggested that there were two SOD2 regulatory states among the ECM-attached. cells (Janes et al. (2010) *Nat Methods* 7(4):311-317; Wang et al. (2011) *Proc Natl Acad Sci U S A* 108(40):E803-812). To apply maximum-likelihood inference, SOD2 expression was deeply sampled by quantitative polymerase chain reaction (qPCR) in 81 random samples of 10 ECM-attached cells (FIG. 5A, left). Stochastic samples of SOD2 were collected as previously described (Wang & Janes (2013) *Nat Protoc* 8(2):282-301; Janes et al. (2010) *Nat Methods* 7(4):311-317; Wang et al. (2011) *Proc Natl Acad Sci U S A* 108(40):E803-812). Briefly, 3D cultures were snap-frozen and sectioned at day 10 of morphogenesis. Random 10-cell samples of ECM-attached acinar cells were achieved by laser-capture microdissection from cryosections. The RNA collected from these samples was amplified with a custom small-sample mRNA amplification procedure, reverse transcribed, and quantified by qPCR (Wang & Janes (2013) *Nat Protoc* 8(2):282-301; Janes et al. (2010) *Nat Methods* 7(4):311-317; Wang et al. (2011) *Proc Natl Acad Sci U S A* 108(40):E803-812).

Using these data, the likelihood of the LN-LN and EXP-LN models were maximized. The relaxed LN-LN model was also maximized, which allowed each regulatory state to have its own log-SD ($\sigma_1$ and $\sigma_2$). The three estimates were compared using Bayesian information criterion (BIC) score to calculate the quality of the fit relative to the number of inferred parameters (Table 1). The best overall estimate was the mixture model that parameterized two distinct regulatory states with the lowest BIC score.

TABLE 1

| | Mixture model | | |
|---|---|---|---|
| | LN-LN | Relaxed LN-LN | EXP-LN |
| SOD2 | <u>183</u> | 165[a] | 184 |
| Infrequent cluster (FIG. 10A) | <u>2286</u> | 2296 | 2373 |
| Rare cluster (FIG. 10B) | <u>440</u> | 454 | 580 |
| IL18 cluster (FIG. 15A) | <u>308</u>[b] | 311 | 515 |
| EEF1A1 cluster (FIG. 15B) | <u>780</u> | 1087 | 875 |
| DDR1 cluster (FIG. 15C) | <u>898</u> | 972 | 1090 |
| SERPINB1 cluster (FIG. 15D) | <u>910</u> | 922 | 967 |
| Very-rare cluster (FIG. 17A) | −17 | <u>−37</u>[c] | 14 |

Minimum scores indicating best fit are underlined.
LN, lognormal;
EXP, exponential.
[a] Relaxed LN-LN was excluded here because the two log-means associated with this inference were less than twofold different from one another. A constrained optimization of this model (see Methods) yielded F = 24.3% with BIC = 180.
[b] Constrained optimization of this model yielded F = 5.1% with BIC = 309.
[c] Constrained optimization of this model yielded F = 2.3% with BIC = −35.

For the 10-cell measurements of SOD2 expression, the LN-LN mixture was slightly preferred over the EXP-LN mixture (FIG. 5A, right, and Table 1). The inability to discriminate clearly between these two models was likely caused by the basal regulatory state, which could be described as an exponential distribution ($\lambda$=46) or with a lognormal distribution with a very small log-mean ($\mu_2$=−4.1) given the sampling data. Regardless, the two models predicted similar SOD2 expression frequencies among ECM-attached cells: 23% (13-33%) for the LN-LN mixture vs. 19% (12-27%) for the EXP-LN mixture.

C. Validating Maximum-Likelihood Inferences of SOD2

Figure 5C:
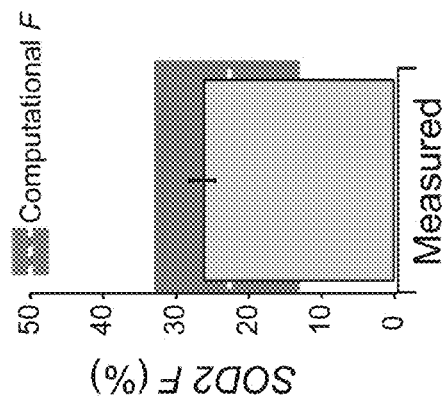
FIG. 5C shows the percentage of cells showing high expression of SOD2 by RNA FISH (gray bar) compared with the maximum-likelihood estimate of F (white dashed).
Figure 5B:
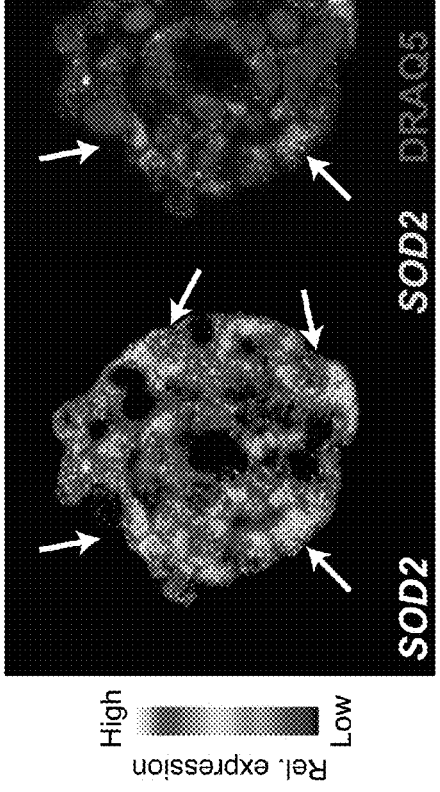
FIG. 5B shows a representative RNA FISH image of endogenous SOD2 expression.

To determine the accuracy of this shared prediction, F was directly measured in 3D spheroids by RNA fluorescence in situ hybridization (RNA FISH) (FIG. 5B). MCF10A-5E 3D cultures were processed for RNA FISH as previously described (Janes et al. (2010) *Nat Methods* 7(4):311-317; Wang et al. (2011) *Proc Natl Acac Sci U S A* 108(40):E803-812). Digoxigenin or dinitrophenol-labeled riboprobes for the genes of interest were cloned, synthesized, and validated as previously described (Janes et al. (2010) *Nat Methods* 7(4):311-317; Wang et al. (2011) *Proc Natl Acad Sci U S A* 108(40):E803-812).

MCF10A-5E 3D cultures were processed for immunofluorescence as previously described (Wang et al. (2011) *Proc Natl Acad Sci U S A* 108(40):E803-812). Sections were stained for IRF2 (1:200; Santa Cruz) and E-cadherin (1:500; BD Transduction Laboratories) and counterstained with DAPI to visualize nuclei. Experimental estimates of F were measured by calculating the number of ECM-attached cells with strong fluorescent signal over basal levels of the probe divided by the entire ECM-attached population in a given tissue section.

RNA FISH sections or whole-mount stained 3D cultures were imaged with a 40×, 1.3 NA oil objective on a Nikon TE-2002-E2 inverted confocal microscope with one 488 nm Ar laser and two HeNe lasers with excitation wavelengths of 543 and 632 nm (Melles Griot). Wheat germ agglutinin (WGA) conjugated to Alexa Fluor 488 (Molecular Probes) was imaged using a 488 nm excitation laser and bandpass emission filter of 515-530 nm. RNA FISH probes and phosphorylated Rb immunofluorescence samples were imaged using a 543 nm excitation laser and bandpass emission filter of 565-615 nm. DRAQ5 nuclear counterstains and loading control riboprobes were imaged using a 632 nm excitation filter and 650 nm long-pass emission filter. Laser gains were adjusted to avoid widespread saturation of the photomultiplier tubes during imaging.

Individual ECM-attached cells were scored manually by fluorescence intensity. Experimental estimates of F were measured by calculating the number of ECM-attached cells with strong fluorescent signal over basal levels of the probe divided by the entire ECM-attached population in a given tissue section. At least 150 ECM-attached cells were scored per slide.

Scoring individual cells with high SOD2 fluorescence, an expression frequency of ~26% was calculated. This measurement closely agreed with the inferred parameter of the LN-LN mixture (the better scoring model; FIG. 5C and Table 1) and lay within the estimated CI of the EXP-LN mixture. By resampling the 10-cell SOD2 data, it was determined that at least 50 Observations were required to arrive at an accurate result (FIG. 6C), confirming the estimates using simulated data described above (FIG. 6A and FIG. 6B).The SOD2 parameterization suggested that maximum-likelihood inference could correctly extract single-cell information from 10-cell sampling data.

Example 4

Maximum-likelihood Inference of Coordinated Stochastic Transcriptional Profiles

A. Extending the Maximum-Likelihood Inference to Coexpression Clusters

Programs of gene expression are often controlled by common upstream factors that enforce the regulatory state. Thus, it was reasoned that coordinated single-cell gene programs would be the product of an overarching regulatory heterogeneity characterized by a shared F. If true, then it should be possible to estimate the expression frequency more confidently and with fewer samples by extending maximum-likelihood inference to gene clusters with coordinated 10-cell fluctuations.

RNA was collected from 3D cultures and process as described above. Expression was quantified using microarrays. Microarray-based expression clusters were identified based on correlate expression fluctuations as previously described (Loo et al. (2009) *J Cell Biol* 187(3):375-384; Wang et al. (2011) *Proc Natl Acad Sci U S A* 108(40):E803-812).

The maximum-likelihood inference approach described above was extended as follows (FIG. 9). First, each gene within the cluster was assigned its own $\mu_1$ and $\mu_2$ for the LN-LN mixture (or $\mu$ and $\lambda$ for the EXP-LN mixture) to account for gene-to-gene differences in expression level and detection sensitivity. Next, it was assumed that the genes within a cluster share a common F and $\sigma$ (or F, $\sigma_1$, and $\sigma_2$ in the relaxed LN-LN mixture), implying a shared mechanism of regulation (Wang et al (2011) *Proc Natl Acad Sci U S A* 108(40):E803-812; Stewart-Ornstein et al. (2012) *Mol Cell* 45(4):483-493). Therefore, each mixture model of a cluster of g genes involved 2g+2 or 2g+3 parameters. Even for small gene programs (g≤10), this parameter search space was too large for nonconvex optimization methods to maximize the global likelihood function quickly. The high-dimensional nonconvex global optimization problem was solved as described above in Example 2. To increase the speed and efficiency of estimation, the cluster was broken down into smaller four-gene subgroups to infer log-means for each gene in the subgroup together with the local estimates for F, $\sigma$, and $\lambda$ (FIG. 9, steps 1 and 2). After log-means were locally estimated, the remaining parameters were globally inferred by remaximizing the likelihood function for the entire gene cluster while retaining the local gene-specific estimates of $\mu_1$ and $\mu_2$ (LN-LN) mixture or $\mu$ (EXP-LN mixture) (FIG. 9, steps 3 and 4). As before, selection of the LN-LN, relaxed LN-LN, and EXP-LN mixture model was made according to the lowest BIC score (Table 1). This revised formulation of maximum-likelihood inference enabled accurate and confident estimates of the expression frequency while requiring only approximately one-third of the sample size (FIG. 11).

B. Test of Maximum-Likelihood Inference on Coexpression Clusters

Figure 12:
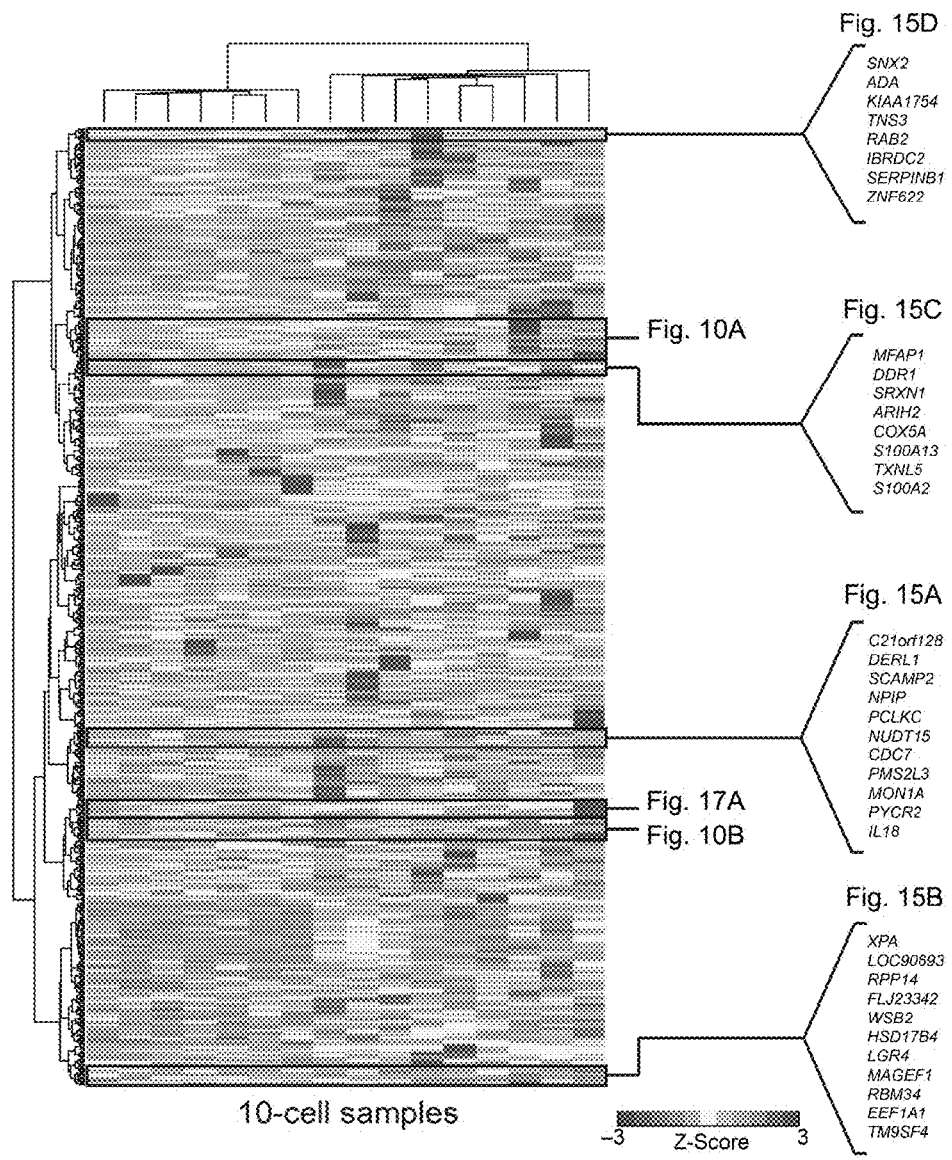
FIG. 12 shows heterogeneously coregulated transcriptional programs parameterized by maximum-likelihood inference.

The extension of the maximum-likelihood inference was tested by extracting from an earlier study by Janes et al. two coexpression clusters that were completely uncharacterized (Janes et al. (2010) *Nat Methods* 7(4):311-317) (FIG. 12). These clusters contained one to two dozen genes with strongly coordinated expression fluctuations across 16 samples of 10 ECM attached cells, but the patterns of fluctuation were markedly different (FIG. 10A and FIG. 10B). Accordingly, when the parameters for the two dusters were inferred, the model predicted two very different expression frequencies. The first "infrequent" gene cluster was predicted to be up-regulated in ~25% of the ECM-attached population (FIG. 10A). The LN-LN mixture model was preferred over the EXP-LN or relaxed LN-LN mixtures (Table 1), although all three models converged upon similar values for F. By contrast, the expression frequency of the "rare" second cluster was predicted to be ~10% by the LN-LN mixture (FIG. 10B), which was the best scoring model of the three (Table 1). The parameterization of the two clusters by the disclosed methods emphasizes the mosaicked regulatory states that evolve even in a very simple model of tissue architecture (Janes et al. (2010) *Nat Methods* 7(4):

311-317; Debnath et al. (2003) *Methods* 30(3):256-268; Wang et al. (2012) *Wiley Interdiscip Rev Syst Biol Med* 4(1):51-78).

To test if the predicted values of F were accurate within the coexpressed clusters, riboprobes for 4-5 genes in each cluster were designed and validated and their frequency of high expression was quantified by RNA FISH (FIG. 13A and FIG. 13B). For probe validation images, antisense and sense control images were exposure matched and scaled to identical linear ranges of intensity display. Representative images of riboprobe staining and pRb staining were scaled to highlight regions of strong staining.

Figure 14A:
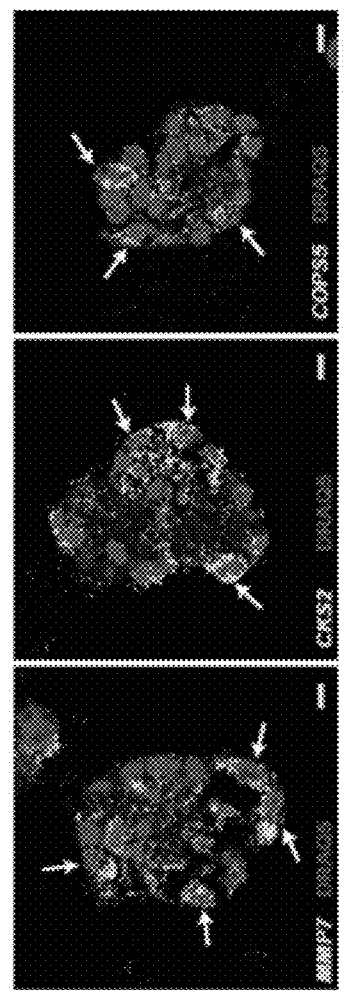
FIG. 14A shows RNA FISH validation of gene expression frequencies. Representative RNA FISH images of genes in the infrequent duster at day 10 of MCF10A-5E 3D morphogenesis.
Figure 14B:
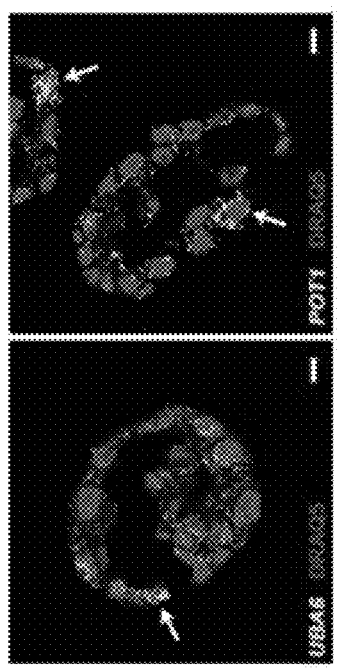
FIG. 14B shows RNA FISH validation of gene expression frequencies. Representative RNA FISH images of genes in the rare cluster (B) at day 10 of MCF10A-5E 3D morphogenesis.

Transcripts in the infrequent expression cluster were strongly expressed in 3-5 ECM-attached cells per acinus cross-section (FIG. 10C, FIG. 10E, and FIG. 14A), yielding an average expression frequency of 25%. Conversely, genes in the rare expression cluster (FIG. 10D, FIG. 10F, and FIG. 14B) were strongly expressed in 1-2 ECM-attached cells per acinus cross-section, consistent with an expression frequency of ~10%. The expression frequencies of both clusters closely agreed with the inferred F parameters, suggesting that our extended inference approach was effective and accurate.

The estimates of expression frequency were evaluated more broadly by selecting four additional clusters from the same dataset for parameterization (FIG. 12) (Janes et al. (2010) *Nat Methods* 7(4):311-317). The clusters showed distinct fluctuation patterns and consequently led to F inferences that ranged from less than 5% to greater than 25% (FIGS. 15A-D, upper). The riboprobes were validated for a representative gene in each cluster and scored the expression frequency (FIGS. 15 A-D, lower, and FIG. 13C). Together with the earlier clusters, a strong correlation between the expression frequency inferred computationally and the manual counts obtained by RNA FISH (R=0.89, FIG. 15E) was observed. Manual counts were obtained as described above.

Figure 16:
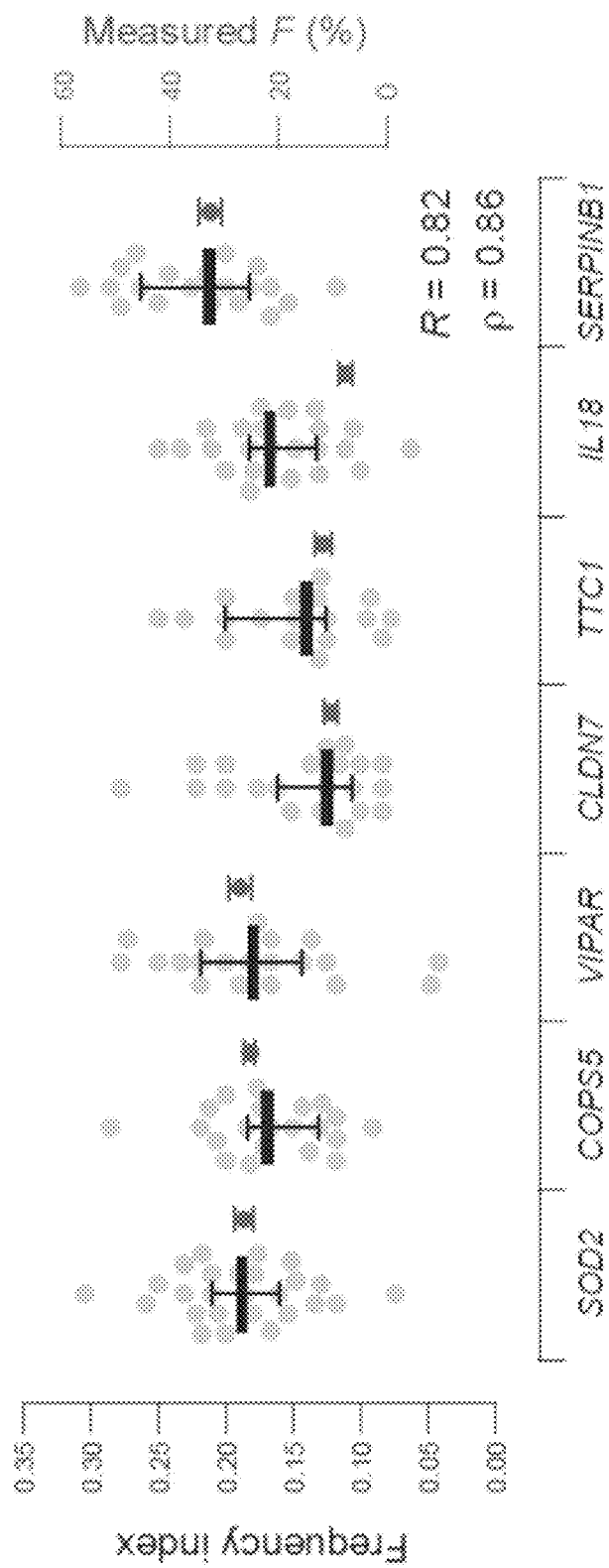
FIG. 16 shows that manually scored expression frequencies correlate with a digitally quantified expression-frequency index.

The accuracy of the manual counts was further confirmed by correlation with an expression-frequency index derived from digital image analysis of segmented acini (FIG. 16). Taken together, these data indicate that maximum-likelihood inference accurately infers single-cell expression frequencies from cluster-wide patterns of 10-cell fluctuations.

Digital scoring of expression frequency index was performed as follows. Multicolor RNA FISH images were acquired with WGA, the riboprobe of interest, and the loading-control riboprobes as described above. Individual ECM-attached cells were manually segmented in ImageJ using the WGA, riboprobe, and loading-control stains to determine cell boundaries. The segmented regions of interest (ROIs) were saved as a single ZIP-file in ImageJ. The pixels within each ROI were extracted and compared against a null pixel distribution comprised of a random set of pixels from segmented cells within the same image. The $85^{th}$-$95^{th}$ percentiles of the cell ROI and the null distribution were compared after bootstrapping each distribution 300 times. A cell was scored in the high regulatory state if the 90% bootstrapped CI of the cell ROI was consistently greater than the 90% bootstrapped CI of the null distribution when evaluated from the $85^{th}$-$95^{th}$ percentile of pixels. Performing the same analysis on the loading-control riboprobes showed that less than 1% of all cells segmented showed detectable differences in total RNA expression. Therefore, the expression-frequency index for a field of view was quantified as the number of cells detected in the high regulatory state divided by the total number of cells segmented. At least 18 fields of view with at least 10 cells per field were acquired for each gene analyzed.

Example 5

Identification of a Peculiar, Very-rare Transcriptional Regulatory State

Figure 17A:
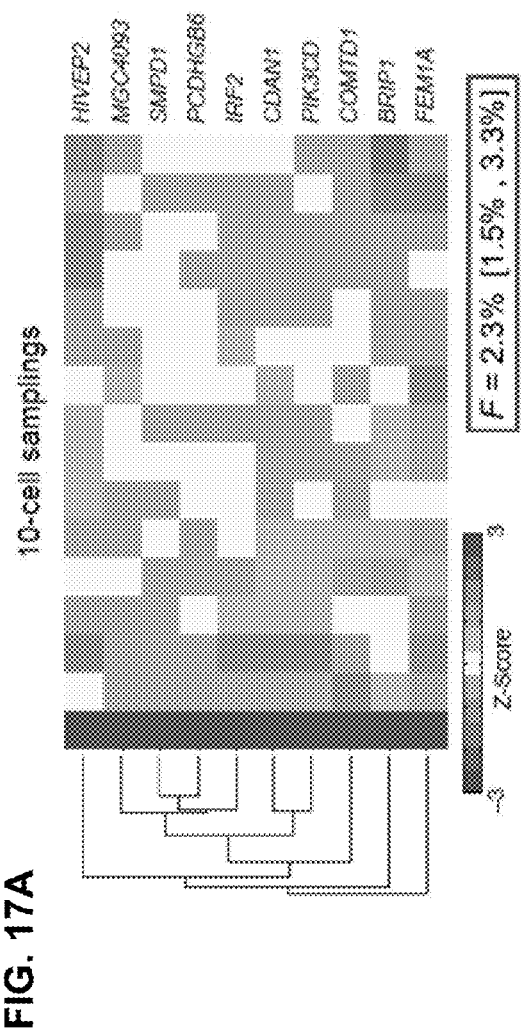
FIG. 17A shows a heat map of clustered 10-cell transcriptional profiles representing a very-rare regulatory state marked by PIK3CD.

Maximum-likelihood inference provides critical information about the state distribution and expression frequency of any gene cluster identified by stochastic profiling to be heterogeneously regulated. As a proof-of-concept application, we screened gene clusters from the 3D profiling data (Janes et al. (2010) *Nat Methods* 7(4):311-317) to identify unusual regulatory states that warranted follow-up study. One cluster was notable among those surveyed because the predicted expression frequency of the high regulatory state was very rare (F=2.3%). The "very-rare" cluster was also distinguished by its strong concordance with the relaxed LN-LN mixture compared to the alternative mixture models (Table 1). Moreover, the log-mean of the low regulatory state was extremely low ($\mu_2$~−3.3), suggesting that the cluster was at or below detection in the population. Within this coexpression cluster, several genes were strongly associated with breast cancer, including the breast cancer susceptibility gene BRIP1 (alternatively called FANCJ or BACH1 (Seal et al. (2006) *Nat Genet* 38(11):1239-1241), the breast cancer associated gene IRF2 (Doherty et al. (2001) *Ann Surg* 233(5):623-629), and the zinc-finger gene HIVEP2, which is frequently downregulated or mutated in breast cancer (Shah et al. (2012) *Nature* 486(7403):395-399; Fuji et al. (2005) *Breast Cancer Res Treat* 91(2):103-112) (FIG. 17A). We speculated that genes within the cluster were tightly regulated so that they could be activated in a restricted cellular context where their expression was critical.

Figure 17B:
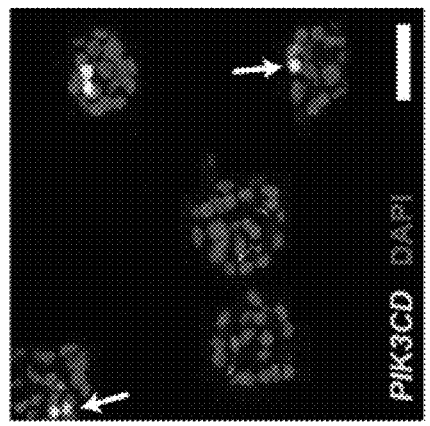
FIG. 17B shows that PIK3CD expression is upregulated during 3D morphogenesis.
Figure 17C:
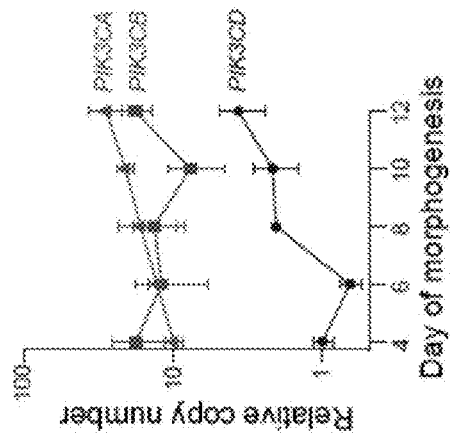
FIG. 17C shows a representative RNA FISH image of PIK3CD expression with DRAQ5 counterstain to visualize nuclei.
Figure 19:
FIG. 19 shows PIK3CG is not expressed in MCF10A-5E cells.
Figure 20A:
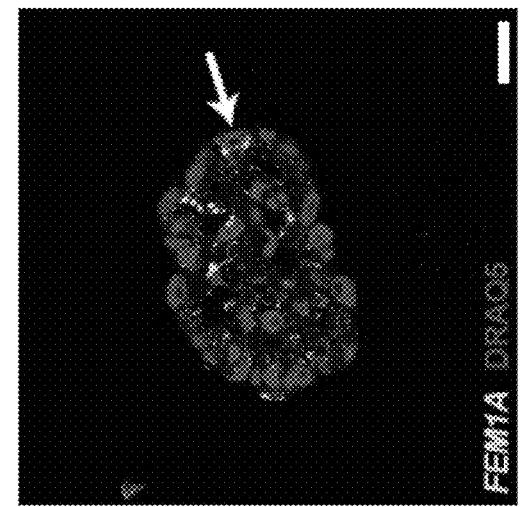
FIG. 20 shows extended validation in ECM-attached cells of a very-rare regulatory state.
Figure 20B:
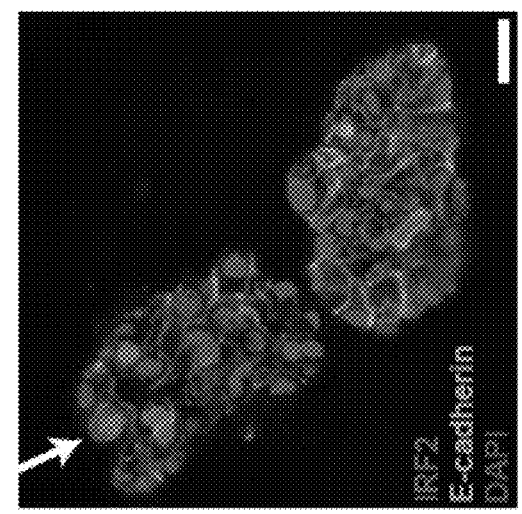
Figure 20C:
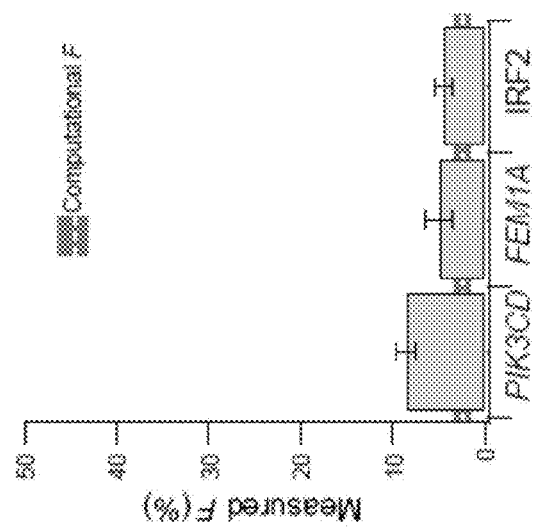

Among the genes in the very-rare cluster, the most intriguing was phosphoinositide-3-kinase (PI3K) isoform PIK3CD (alternatively called p110δ). 3D breast epithelial cultures abundantly express two other PI3K isoforms, PIK3CA and PIK3CB (FIG. 17B and FIG. 19), and it is generally thought that any PI3K isoform can support proliferation and survival (Foukas et al. (2010) *Proc Natl Acad Sci U S A* 107(25): 11381-11386). Nevertheless, the low-copy expression of PIK3CD was transcriptionally upregulated with delayed kinetics compared to the other PI3K isoforms (FIG. 17B), suggesting a unique regulatory mechanism. Expression of PIK3CA, PIK3CB, and PIK3CD was determined by qPCR as described above. Relative copy numbers of PIK3C4, PIK3CB, and PIK3CD were obtained using a common standard of MCF10A-5E genomic DNA A striking pattern was observed when PIK3CD abundance was visualized in single cells by RNA FISH. Most cells lacked PIK3CD or expressed it at very-low levels; however, a sporadic subpopulation of cells (roughly 1-2 cells every other acinus cross-section) was consistently identified with high PIK3CD expression (FIG. 17C and FIG. 13D). The overall frequency of cells in the PIK3CD$^{hi}$ state was somewhat higher than the maximum-likelihood inferences of F for the cluster, but the inferred frequency agreed with the very-rare expression of two other members of the cluster, FEM1A and IRF2 (FIG. 20). Together, these observations pointed to an acute (and likely transient) regulatory event triggering the selective induction of cluster genes in single ECM-attached cells.

A. Perturbation of the Very-Rare Subpopulation

Figure 18C:
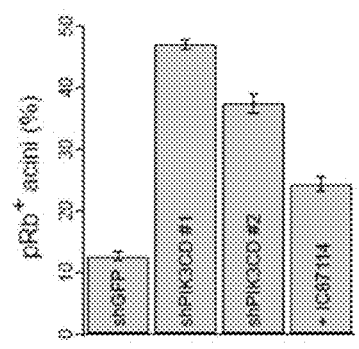
FIG. 18C shows the quantification of proliferating acini in each condition (shGFP, shPIK3CD #1, and shPIK3CD #2 cells or shGFP cells +20 µM p110δ inhibitor IC87114).
Figure 18B:
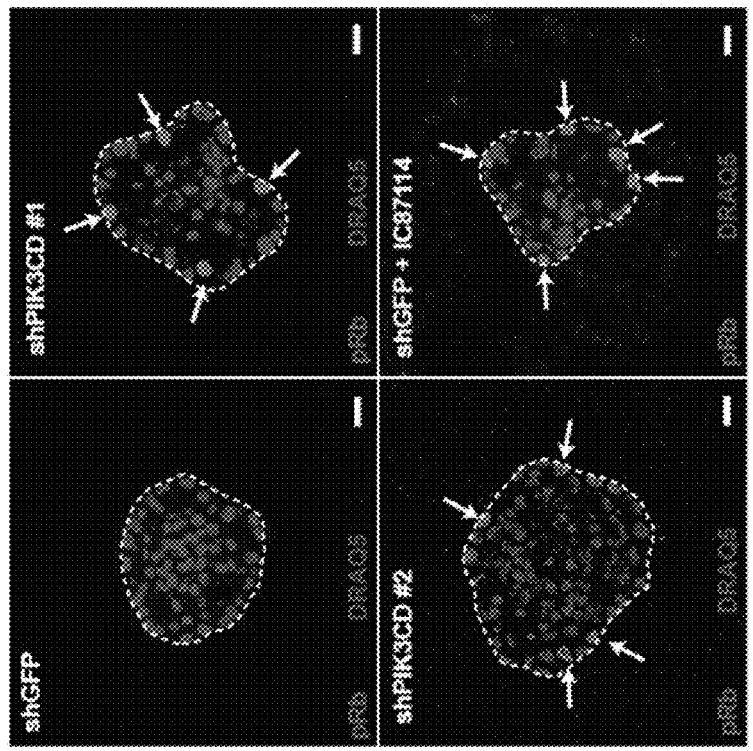
FIG. 18B shows immunofluorescence images demonstrating that disruption of normal PIK3CD regulation elicits a hyperproliferative phenotype in 3D culture.
Figure 18A:
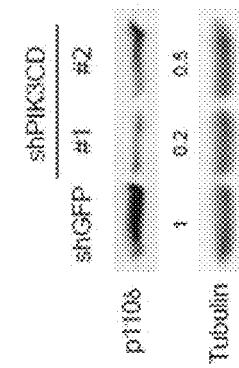
FIG. 18A shows knockdown of p110δ by shRNA.
Figure 21:
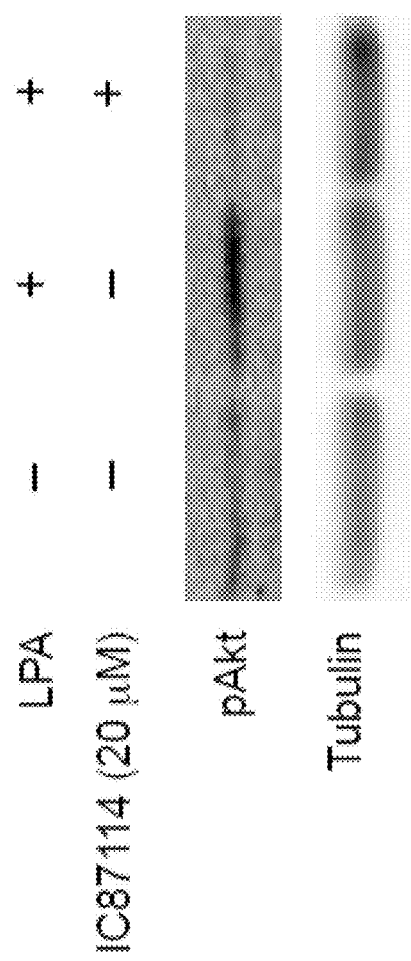
FIG. 21 shows IC87114 inhibits Akt phosphorylation stimulated by p110δ.

We next asked whether PIK3CD was specifically important for normal acinar morphogenesis. To eliminate the very-rare PIK3CD$^{hi}$ subpopulation, p110δ was perturbed by two independent methods: RNA interference and the p110δ-specific small-molecule inhibitor, IC87114 (Knight et al. (2006) Cell 125(4):733-747) (FIG. 18A and FIG. 21). For RNRA interference experiments, small hairpin RNA (shRNA) specific for green fluorescent protein (shGFP), a control, and shRNRA specific for PIK3CD (shPIK3CD) were designed. shRNA sequences against PIK3CD were cloned based on the targeting sequences suggested by the RNAi Consortium, except that the XhoI restriction site in the shRNA loop was changed to a PstI site for easier diagnosis during cloning. shGFP control was used as previously described (Orimo et al. (2005) Cell 121(3):335-348). Primers were annealed at 95° C. in annealing buffer (10 mM Tris-HCl, 100 mM NaCl, 1 mM EDTA) for 5 min on a thermocycler and cooled slowly to room temperature by unplugging the instrument. Annealed primers were phosphorylated in vitro with T4 polynucleotide kinase (New England Biolabs) and then cloned into pLKO.1 puro (Moffat et al. (2006) Cell 124(6):1283-1298) that had been digested with EcoRI and AgeI. Lentiviruses were packaged and transduced into MCF10A-5E cells and selecting with 2 μg/ml puromycin as previously described (Wang et al. (2011) Proc Natl Acad Sci U S A 108(40):E803-812) to produce shGFP and shPIK3CD cell lines. MCF10A (shGFP, and shPIK3CD) cell lines were cultured in 3D as previously described (Debnath et al. (2003) Methods 30(3):256-268). Stable lines were screened for knockdown efficiency by immunoblotting For p110δ inhibitor experiments, 20 μM IC87114 (Calbiochem) was added to the assay medium and replaced every four days. IC87114 inhibitor validation was performed as follows. MCF10A-5E cells were plated in 6-well dishes and cultured in serum-free medium overnight. Wells were pre-treated with or without 20 μM IC87114 (Calbiochem) for one hour and then stimulated with 10 μM lysophosphatidic acid (Sigma-Aldrich) for five minutes. Cells were lysed as previously described (Wang et al. (2011) Proc Natl Acad U S A 108(40):E803-812), and lysates were probed for pAkt levels by immunoblotting.

Immunoblotting was performed as follows. 30-50 μg of clarified cell extract was separated on an 8% or 10% SDS-PAGE gel and transferred to PVDF (Millipore). Membranes were blocked in 0.5×Odyssey blocking buffer (Licor) for one hour and incubated overnight at 4° C. in 0.5× Odyssey blocking buffer with 0.1% Tween containing one of the following primary antibodies: anti-p110δ (1:500; Santa Cruz Biotechnology) or anti-pAkt Ser473 (1:1000; Cell Signaling). Additionally, chicken anti-tubulin (1:20000; Abcam) was added to each primary solution as a loading control. Membranes were washed four times in phosphate buffered saline+0.1% Tween (PBS-T) for five minutes each, and incubated in 0.5×Odyssey+0.1% Tween+0.01% SDS with the following secondary antibodies: goat anti-rabbit 800 (1:20000; Licor) and goat anti-chicken 680 (1:20000; Licor). Membranes were washed four times with PBS-T and once with PBS for five minutes each before imaging with an odyssey detection system (Licor).

Whole-mount immunofluorescence of shGFP and shPIK3CD cultures was performed as previously described (Wang et al. (2011) Proc Natl Acad U S A 108(40):E803-812). Samples were stained for phospho-Rb Ser807/811 (1:200; Cell Signaling) and counterstained with DRAQ5 to visualize nuclei. Samples were scored for pRb-positive acini as before (Wang et al. (2011) Proc Natl Acad Sci U S A 108(40):E803-812).

When shPIK3CD cells were placed in 3D culture, acini were larger and distorted, suggesting a defect in proliferation arrest. Using phosphorylated Rb (pRh) as a proliferative marker, shPIK3CD acini were still cycling after fifteen days of 3D culture when shGFP control acini had quiesced (FIG. 18B and FIG. 18C). Furthermore, when control cells were cultured with IC87114, we observed sustained proliferation that phenocopied PIK3CD knockdown (FIG. 18B and FIG. 18C). These data together indicate that p110δ activity stemming from the very-rare PiK3CD$^{hi}$ regulatory state is critical for normal proliferation arrest of breast epithelia in 3D culture. More broadly, these results with the very-rare cluster illustrate how maximum-likelihood inference can be used to hone in on gene programs with an expression frequency or regulatory pattern of interest

Example 6

Comparison with Alternative Deconvolution Methods

The performance of maximum-likelihood inference was compared to other computational approaches for deconvolving mixed populations (Erkkild et al. (2010) Bioinformatics 26(20):2571-2577; Repsilber et al. (2010) BMC Bioinformatics 11:27; Tolliver et al. (2010) Bioinformatics 26(12): i106-114). The alternative methods invoked different mathematical formalisms—Bayesian statistics (Erkkilä et al. (2010) Bioinformatics 26(20):2571-2577), nonnegative matrix factorization (Repsilber et al. (2010) BMC Bioinformatics 11:27), and principal component analysis (Tolliver et al. (2010) Bioinformatics 26(12):i106-114)—and none had previously been applied to transcriptional profiles of small samples. Using the sampling fluctuations within the infrequent, rare, and very-rare clusters, we attempted inferences of expression frequency and found that all were substantially less accurate than maximum-likelihood inference (Table 2). The comparison illustrates that the disclosed method is uniquely effective at parameterizing transcriptional regulatory states within cell populations.

TABLE 2

| | Stochastic-profiling cluster | | |
|---|---|---|---|
| Method | Infrequent | Rare | Very rare |
| Erkkilä et al.* | 20% | ~0%[†] | ~0%[†] |
| Repsilber et al. | 22% | 60% | 30, 21, 19, 30% |
| Tolliver. et al | 18, 40, 23, 19%[‡] | 59, 7.2, 11, 22% | 30, 21, 19, 30% |
| Maximum-likelihood inference | 25% [24%, 27%][§] | 10% [8.6%, 12%] | 2.3% [1.5%, 3.3%] |
| RNA FISH | 25% [24%, 26%][§] | 10% [9.4%, 12%] | 5.6% [4.7%, 7.3%] |

*Bayesian priors were set to 25%, 10%, and 5% for the infrequent, rare, and very rare clusters, respectively.
[†]The estimated frequency was 2 × 10$^{-12}$%
[‡]A minimum of four subpopulations must be estimated with this deconvolution method.
[§]Bracket denotes 95% CI.
(Erkkilä et al. (2010) Bioinformatics 26(20): 2571-2577; Repsilber et al. (2010) BMC Bioinformatics 11:27; Tolliver et al. (2010) Bioinformatics 26(12): i106-114)

Example 7

Direct Comparison of Single-cell and 10-cell Sampling Strategies

Maximum-likelihood inference reconstructs the single-cell expression distribution without the need to measure single cells. Ignoring the technical challenges of global single-cell methods (Ramskold et al. (2012) *Nat Biotechnol* 30(8):777-782; Wang & Janes (2013) *Nat Protoc* 8(2):282-301; Reiter et al. (2011) *Nucleic Acids Res* 39(8):e124; Janes et al. (2010) *Nat Methods* 7(4):311-317), it should also be theoretically possible to recreate the complete expression distribution by measuring many individual cells. However, it was not clear whether single-cell profiling would be as effective as stochastic profiling when reconstructing from a limited number of one or 10-cell samples, We anticipated that low expression frequencies would be particularly difficult for single-cell methods to characterize because of uncertainty in reliably capturing the rare regulatory state.

To compare single-cell profiling with stochastic profiling, we repeatedly simulated one- or 10-cell measurements of gene clusters with similar characteristics to those previously examined (FIG. 10C, FIG. 10D, FIG. 17A). Measurements were simulated for various gene clusters as described above with either n=1 or n=10, m=12, and k=16 with the mixture model and F specified in Table 2. Values of $\mu_1$, $\mu_2$, $\lambda$, $\mu$, and $\sigma$ were drawn randomly from the individual transcripts comprising the inferences of FIG. 10C, FIG. 10D, and FIG. 15A. Model parameters were inferred as described above with the correct value of n in equations 12 and 14. The inference procedure was repeated 100 times, yielding estimates $\hat{\theta}_i^j$ (j=1, 2, . . . 100) for each true parameter $\theta_i$. This gives the following Monte Carlo estimates of bias, variance, and mean-squared error:

$$\text{Bias}(\hat{\theta}_i) = \frac{1}{100}\sum_{j=1}^{100}\hat{\theta}_i^j - \theta_i$$

$$\text{Var}(\hat{\theta}_i) = \frac{1}{99}\sum_{j=1}^{100}\{\hat{\theta}_i^j - \theta_i\}^2$$

$$MSE(\hat{\theta}_i) = \text{Bias}(\hat{\theta}_i)^2 + \text{Var}(\hat{\theta}_i)$$

The three 12-gene clusters varied in their expression fraction—infrequent (F=25%), rare (F=10%), and very rare (F=5%)—and the very-rare cluster was simulated as an LN-LN mixture or an EXP-LN mixture. When the number of observations was limited to 16 (as in the actual data), we found that maximum-likelihood inference provided superior estimates of F when using 10-cell groups (Table 3). Inferences from simulated observations of 16 single cells showed substantially higher mean squared error (MSE) for all gene clusters when compared to 16 10-cell observations The larger MSE of one-cell inferences was caused by increases in both the bias and variance of the estimate, whose magnitudes depended on the chister characteristics and mixture model. These computational simulations provide an upper bound on performance, because experimental error from actual single-cell experiments (Ramskold et al. (2012) *Nat Biotechnol* 30(8):777-782; Shalek et al. (2013) *Nature* 498 (7453):236-240) should blur the data much more. By collecting a greater total number of cells when observations are limited, maximum-likelihood inference of stochastic 10-cell profiles provides a more-accurate picture of the single-cell distribution than single-cell profiles.

TABLE 3

| True | | | Maximum-likelihood estimate of F | |
|---|---|---|---|---|
| F Mixture | Cells | MSE × $10^{-2}$ | Bias × $10^{-2}$ | Variance × $10^{-2}$ |
| 25%* LN-LN | 1 | 4.32 | −20.76 | 0.01 |
| | 10 | 0.30 | −3.40 | 0.19 |
| 10%† LN-LN | 1 | 2.35 | −2.83 | 2.27 |
| | 10 | 0.19 | 1.37 | 0.17 |
| 5%‡ LN-LN | 1 | 19.73 | 29.09 | 11.27 |
| | 10 | 0.16 | 1.73 | 0.13 |
| 5%§ EXP-LN | 1 | 57.18 | 75.09 | 0.79 |
| | 10 | 4.50 | 0.80 | 1.77 |

MSE, bias, and variance were calculated across 100 simulations of 16 observations.
F is defined from 0 to 100 × $10^{-2}$.
MSE = bias$^2$ + variance.
*Parameter set: $\mu_1$ = [0.7-2.0], $\mu_2$ = [−1.5-−0.3], $\sigma$ = 0.5.
†Parameter set: $\mu_1$ = [−1.5-−0.2], $\mu_2$ = [−3.8-−2.0], $\sigma$ = 0.5.
‡Parameter set: $\mu_1$ = [−2.0-−0.9], $\mu_2$ = [−3.8-−3.1], $\sigma$ = 0.5.
§Parameter set: $\mu$ = [−0.9-−2.0], $\lambda$ = [11-145], $\sigma$ = 2.3.

The above description discloses several methods and systems of the present disclosure. This disclosure is susceptible to modifications in the methods and systems, as well as alterations. Such modifications will become apparent to those skilled in the art from a consideration of this disclosure or practice of the present disclosure described herein. Consequently, it is not intended that this disclosure be limited to the specific embodiments disclosed herein, but that it cover all modifications and alternatives coming within the true scope and spirit of the disclosure.

The invention claimed is:

1. A method of detecting single-cell gene expression characteristics, comprising:
   a) providing a mixed population of cells containing cell-to-cell expression heterogeneities and two distinct regulatory states of one or more individual genes in each cell of the cell population, wherein one of the regulatory states of an individual gene is a basal state and the other regulatory state of the individual gene is an induced state;
   b) providing 50-100 random samples from the mixed population of cells, wherein each random sample comprises a pool of about 10 cells;
   c) measuring expression of the individual gene in each of the random samples; and
   d) determining by maximum-likelihood inference the single-cell gene expression distribution of the individual gene across the population of cells;
      wherein the basal state and the induced state can each be approximated by a lognormal distribution;
      and wherein the basal state and the induced state lognormal distributions are characterized by the following parameters:
   $\mu_2$ is the log-mean expression of the basal regulatory state;
   $\mu_1$ is the log-mean expression of the induced regulatory state;
   $\sigma$ is the common log-standard deviation of the basal state and the induced regulatory state;
   and F is the probability that a single cell is in the induced regulatory state;
      and wherein the maximum-likelihood inference is determined as follows:

$$f_{mixture}(g) = F \cdot f_1(g) + (1-F) \cdot f_2(g),$$

where (g) is a transcript expressed at a low level in the basal state and at a higher level in the induced state, and where $f_1^{(g)}$ and $f_2^{(g)}$ are defined as:

$$f_v^{(g),LN-LN}(x) = \frac{1}{\sqrt{2\pi}\,\sigma x} \cdot \exp\left\{-\frac{[\log(x)-\mu_v^{(g)}]^2}{2\sigma^2}\right\}$$

for $x > 0$ and $v \in \{1, 2\}$, where the $i^{th}$ random sample of transcript g, $Y_i^{(g)}$, is the sum of n independent single-cell expression measurements:

$$Y_i^{(g)} = \sum_{j=1}^{n} X_{ij}^{(g)},$$

where $X_{ij}^{(g)}$ is the expression of transcript g in the $j^{th}$ cell of the $i^{th}$ random sample,
where the random sample $Y_i^{(g)}$ describing the n-cell mixture is defined as:

$$f_n^{LN-LN}(y \mid F, \mu_1^{(g)}, \mu_2^{(g)}, \sigma) = \sum_{j=0}^{n} \binom{n}{j} F^j (1-F)^{n-j} f_{(j,n-j)}^{(g),LN-LN}(y),$$

where $\binom{n}{j} F^j (1-F)^{n-j}$ is the binomial selection of cells from the basal or induced states with probabilities F and 1-F, respectively,
where $f_{(j,n-j)}^{(g)}$ is the density of a sum $Z_1 + \ldots + Z_n$ of independent random variables representing the n-cell draw from the following mixture model:

$$Z_c^{LN-LN} = \begin{cases} LN(\mu_1^{(g)}, \sigma^2) & \text{if } 1 \leq c \leq j \\ LN(\mu_2^{(g)}, \sigma^2) & \text{if } j < c \leq n \end{cases}$$

and where the probability density function of the sum of lognormally distributed random variables is approximated and applied to the mixture model.

2. The method of claim 1, wherein the number of cells in each random sample is 10.

3. The method of claim 1, wherein the number of random samples is 50.

4. The method of claim 1, further comprising a step of approximating single cell expression frequency.

5. A method of detecting single-cell gene expression characteristics, comprising:
   a) providing a mixed population of cells containing cell-to-cell expression heterogeneities and two distinct regulatory states of one or more individual genes in each cell of the cell population, wherein one of the regulatory states of an individual gene is a basal state and the other regulatory state of the individual gene is an induced state;
   b) providing 50-100 random samples from the mixed population of cells, wherein each random sample comprises a pool of about 10 cells;
   c) measuring expression of the individual gene in each of the random samples; and
   d) determining by maximum-likelihood inference the single-cell gene expression distribution of the individual gene across the population of cells;
      wherein the basal state is approximated by an exponential distribution and the induced state is approximated by a lognormal distribution;
      and wherein the basal state and the induced state exponential and lognormal distributions are characterized by the following parameters:
   $\lambda$ is the rate parameter for the basal state;
   $\mu$ is the log-mean expression of the induced state;
   $\sigma$ is the common log-standard deviation of the basal state and the induced state;
   and F is the probability that a single cell is in the induced state,
      and wherein the maximum-likelihood inference is determined as follows:

$$f_{mixture}^{(g)} = F \cdot f_1^{(g)} + (1-F) \cdot f_2^{(g)},$$

where (g) is a transcript expressed at a low level in the basal state and at a higher level in the induced state,
and where $f_1^{(g)}$ and $f_2^{(g)}$ are defined as:

$$f_2^{(g),EXP-LN}(x) = \lambda^{(g)} \cdot \exp(-\lambda^{(g)} \cdot x) \quad \text{for } x \geq 0$$

$$f_1^{(g),EXP-LN}(x) = \frac{1}{\sqrt{2\pi}\sigma x} \cdot \exp\left\{-\frac{[\log(x)-\mu^{(g)}]^2}{2\sigma^2}\right\} \quad \text{for } x > 0,$$

where the $i^{th}$ random sample of transcript g, $Y_i^{(g)}$, is the sum of n independent single-cell expression measurements:

$$Y_i^{(g)} = \sum_{j=1}^{n} X_{ij}^{(g)},$$

where $X_{ij}^{(g)}$ is the expression of transcript g in the $j^{th}$ cell of the $i^{th}$ random sample,
where the random sample $Y_i^{(g)}$ describing the n-cell mixture is defined as:

$$f_n^{EXP-LN}(y \mid F, \mu^{(g)}, \lambda^{(g)}, \sigma) = \sum_{j=0}^{n} \binom{n}{j} F^j (1-F)^{n-j} f_{(j,n-j)}^{(g),EXP-LN}(y),$$

where $\binom{n}{j} F^j (1-F)^{n-j}$ is the binomial selection of cells from the basal or induced states with probabilities F and 1-F, respectively,
where $f_{(j,n-j)}^{(g)}$ is the density of a sum $Z_1 + \ldots + Z_n$ of independent random variables representing the n-cell draw from the following mixture model:

$$Z_c^{EXP-LN} = \begin{cases} LN(\mu^{(g)}, \sigma^2) & \text{if } 1 \leq c \leq j \\ EXP(\lambda^{(g)}) & \text{if } j < c \leq n \end{cases},$$

where the probability density function of the mixture model is the convolution of a lognormal and an exponential density.

6. The method of claim 5, wherein the number of cells in each random sample is 10.

7. The method of claim 5, wherein the number of random samples is 50.

8. The method of claim 5, further comprising a step of approximating single cell expression frequency.

9. A method of detecting single-cell gene expression characteristics of a gene cluster comprising a plurality of individual genes with a common expression characteristic, the steps comprising:
   a) providing a mixed population of cells containing cell-to-cell expression heterogeneities and two distinct regulatory states of one or more individual genes of the gene cluster in each cell of the cell population, wherein one of the regulatory states of an individual gene is a basal state and the other regulatory state of the individual gene is an induced state;
   b) providing random samples from the mixed population of cells, wherein each random sample comprises a pool of about 10 cells;
   c) measuring expression of the individual gene in each of the random samples; and
   d) determining by maximum-likelihood inference the single-cell gene expression distribution of the gene cluster across the population of cells,
      wherein the basal state and the induced state can each be approximated by a lognormal distribution,
      and wherein the basal state and the induced state lognormal distributions are characterized by the following parameters:
   $\mu_2$ is the log-mean expression of the basal regulatory state;
   $\mu_1$ is the log-mean expression of the induced regulatory state;
   $\sigma$ is the common log-standard deviation of the basal state and the induced regulatory state;
   and F is the probability that a single cell is in the induced regulatory state,
      and wherein the maximum-likelihood inference is determined as follows:

$$f_{mixture}^{(g)} = F \cdot f_1^{(g)} + (1-F) \cdot f_2^{(g)},$$

here (g) is a transcript expressed at a low level in the basal state and at a higher level in the induced state,
and where $f_1^{(g)}$ and $f_2^{(g)}$ are defined as:

$$f_v^{(g),LN-LN}(x) = \frac{1}{\sqrt{2\pi}\,\sigma x} \cdot \exp\left\{-\frac{[\log(x) - \mu_v^{(g)}]^2}{2\sigma^2}\right\}$$

for $x > 0$ and $v \in \{1, 2\}$, where the $i^{th}$ random sample of transcript g, $Y_i^{(g)}$, is the sum of n independent single-cell expression measurements:

$$Y_i^{(g)} = \sum_{j=1}^{n} X_{ij}^{(g)},$$

where $X_{ij}^{(g)}$ is the expression of transcript g in the $j^{th}$ cell of the $i^{th}$ random sample,
where the random sample $Y_i^{(g)}$ describing the n-cell mixture is defined as:

$$f_n^{LN-LN}(y \mid F, \mu_1^{(g)}, \mu_2^{(g)}, \sigma) = \sum_{j=0}^{n} \binom{n}{j} F^j (1-F)^{n-j} f_{(j,n-j)}^{(g),LN-LN}(y),$$

where $\binom{n}{j} F^j (1-F)^{n-j}$ is the binomial selection of cells from the basal or induced states with probabilities F and 1-F, respectively,
where $f_{(j,\,n-j)}^{(g)}$ is the density of a sum $Z_1 + \ldots + Z_n$ of independent random variables representing the n-cell draw from the following mixture model:

$$Z_c^{LN-LN} = \begin{cases} LN(\mu_1^{(g)}, \sigma^2) & \text{if } 1 \leq c \leq j \\ LN(\mu_2^{(g)}, \sigma^2) & \text{if } j < c \leq n \end{cases}$$

where the probability density function of the sum of lognormally distributed random variables is approximated and applied to the mixture model,
and where the log-likelihood function for the model parameters given k random n-cell samples is:

$$\ell^{LN-LN}(F, \underline{\mu_1}, \underline{\mu_2}, \sigma) = \sum_{g=1}^{m} \sum_{i=1}^{k} \log[f_n^{LN-LN}(y_i^{(g)} \mid F, \mu_1^{(g)}, \mu_2^{(g)}, \sigma)],$$

where the gene cluster is m transcripts,
where $\mu_1$ and $\mu_2$, are vectors containing the transcript-specific log-means for the two regulatory states: $\underline{\mu_1} = (\mu_1^{(1)}, \ldots, \mu_1^{(m)})$ and $\underline{\mu_2} = (\mu_2^{(1)}, \ldots, \mu_2^{(m)})$,
and where the log-likelihood function assumes that the expression levels of each transcript are independent as defined by the specific mixture model and F.

10. The method of claim 9, wherein the individual genes of the gene cluster are grouped into four-gene subgroups to infer log-means for each gene in the subgroup and local estimates of F and $\sigma$.

11. The method of claim 9, wherein the number of cells in each random sample is 10.

12. The method of claim 9, wherein the number of random samples is less than 50.

13. The method of claim 9, further comprising a step of approximating single cell expression frequency.

14. A method of detecting single-cell gene expression characteristics of a gene cluster comprising a plurality of individual genes with a common expression characteristic, the steps comprising:
   a) providing a mixed population of cells containing cell-to-cell expression heterogeneities and two distinct regulatory states of one or more individual genes of the gene cluster in each cell of the cell population, wherein one of the regulatory states of an individual gene is a basal state and the other regulatory state of the individual gene is an induced state;
   b) providing random samples from the mixed population of cells, wherein each random sample comprises a pool of about 10 cells;
   c) measuring expression of the individual gene in each of the random samples; and d) determining by maximum-likelihood inference the single-cell gene expression distribution of the gene cluster across the population of cells;
   wherein the basal state is approximated by an exponential distribution and the induced state is approximated by a lognormal distribution;
   and wherein the basal state and the induced state exponential and lognormal distributions are characterized by the following parameters:

$\lambda$ is the rate parameter of an individual gene in the basal state;

$\mu$ is the log-mean expression of an individual gene in the induced state;

$\sigma$ is the common log-standard deviation of the basal state and the induced state;

and F is the probability that a single cell is in the induced state,
   and wherein the maximum-likelihood inference is determined as follows:

the single-cell expression for transcript g follows the probability density function:

$$f_{mixture}^{(g)} = F \cdot f_1^{(g)} + (1-F) \cdot f_2^{(g)},$$

where (g) is a transcript expressed at a low level in the basal state and at a higher level in the induced state, and where $f_1^{(g)}$ and $f_2^{(g)}$ are defined as:

$$f_2^{(g),EXP-LN}(x) = \lambda^{(g)} \cdot \exp(-\lambda^{(g)} \cdot x) \quad \text{for } x \geq 0$$

$$f_1^{(g),EXP-LN}(x) = \frac{1}{\sqrt{2\pi}\sigma x} \cdot \exp\left\{-\frac{[\log(x) - \mu^{(g)}]^2}{2\sigma^2}\right\} \quad \text{for } x > 0,$$

where the $i^{th}$ random sample of transcript g, $Y_i^{(g)}$, is the sum of n independent single-cell expression measurements:

$$Y_i^{(g)} = \sum_{j=1}^{n} X_{ij}^{(g)},$$

where $X_{ij}^{(g)}$ is the expression of transcript g in the $j^{th}$ cell of the $i^{th}$ random sample, where the random sample $Y_i^{(g)}$ describing the n-cell mixture has the probability density function:

$$f_n^{EXP-LN}(y \mid F, \mu^{(g)}, \lambda^{(g)}, \sigma) = \sum_{j=0}^{n} \binom{n}{j} F^j (1-F)^{n-j} f_{(j,n-j)}^{(g),EXP-LN}(y),$$

where $\binom{n}{j} F^j (1-F)^{n-j}$ is the binomial selection of cells from the basal or induced states with probabilities F and 1-F, respectively, where $f_{(j,n-j)}^{(g)}$ is the density of a sum $Z_1 + \ldots + Z_n$ of independent random variables representing the n-cell draw from the following mixture model:

$$Z_c^{EXP-LN} = \begin{cases} LN(\mu^{(g)}, \sigma^2) & \text{if } 1 \leq c \leq j \\ LN(\lambda^{(g)}) & \text{if } j < c \leq n \end{cases},$$

where the probability density function of the mixture model is the convolution of a lognormal and an exponential density, and where the log-likelihood function for the model parameters given k random n-cell samples is:

$$l^{EXP-LN}(F, \underline{\mu}, \underline{\lambda}, \sigma) = \sum_{g=1}^{m} \sum_{i=1}^{k} \log\left[f_n^{EXP-LN}\left(y_i^{(g)} \mid F, \mu^{(g)}, \lambda^{(g)}, \sigma\right)\right],$$

where the gene cluster is m transcripts, where $\underline{\mu}$, and $\underline{\lambda}$ are vectors containing the transcript-specific log-means for the two regulatory states: $\underline{\mu} = (\mu^{(1)}, \ldots, \mu^{(m)})$, and $\underline{\lambda} = (\lambda^{(1)}, \ldots, \lambda^{(m)})$, and where the log-likelihood function assumes that the expression levels of each transcript are independent as defined by the specific mixture model and F.

15. The method of claim 14, wherein the individual genes of the gene cluster are grouped into four-gene subgroups to infer log-means for each gene in the subgroup and local estimates of F and $\sigma$.

16. The method of claim 14, wherein the number of cells in each random sample is 10.

17. The method of claim 14, wherein the number of random samples is less than 50.

18. The method of claim 14, further comprising a step of approximating single cell expression frequency.

* * * * *

UNITED STATES PATENT AND TRADEMARK OFFICE
CERTIFICATE OF CORRECTION

PATENT NO. : 10,453,555 B2
APPLICATION NO. : 15/000448
DATED : October 22, 2019
INVENTOR(S) : Kevin Janes et al.

It is certified that error appears in the above-identified patent and that said Letters Patent is hereby corrected as shown below:

In the Claims

Claim 1, Column 33, Line 9, "thei$^{th}$" should read --the i$^{th}$--.

Claim 1, Column 33, Line 37, "draw from" should read --drawn from--.

Claim 5, Column 34, Line 30, "thei$^{th}$" should read --the i$^{th}$--.

Claim 5, Column 34, Line 58, "draw from" should read --drawn from--.

Claim 9, Column 35, Line 55, "thei$^{th}$" should read --the i$^{th}$--.

Claim 9, Column 36, Line 15, "draw from" should read --drawn from--.

Claim 14, Column 37, Line 36, "thei$^{th}$" should read --the i$^{th}$--.

Claim 14, Column 38, Line 14, "draw from" should read --drawn from--.

Claim 14, Column 38, Line 19, "LN($\lambda^{(g)}$)" should read --EXP($\lambda^{(g)}$)--.

Signed and Sealed this
Thirty-first Day of May, 2022

Katherine Kelly Vidal
*Director of the United States Patent and Trademark Office*